(12) United States Patent
Nagase et al.

(10) Patent No.: US 11,673,867 B2
(45) Date of Patent: Jun. 13, 2023

(54) SULFONAMIDE DERIVATIVE OR PHARMACEUTICALLY ACCEPTABLE ACID-ADDITION SALT

(71) Applicants: University of Tsukuba, Tsukuba (JP); BOARD OF REGENTS, THE UNIVERSITY OF TEXAS SYSTEM, Austin, TX (US)

(72) Inventors: Hiroshi Nagase, Tsukuba (JP); Tsuyoshi Saitoh, Tsukuba (JP); Masashi Yanagisawa, Tsukuba (JP); Yoko Irukayama, Tsukuba (JP)

(73) Assignees: University of Tsukuba, Tsukuba (JP); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 60 days.

(21) Appl. No.: 16/772,314

(22) PCT Filed: Dec. 11, 2018

(86) PCT No.: PCT/JP2018/045523
§ 371 (c)(1),
(2) Date: Jun. 12, 2020

(87) PCT Pub. No.: WO2019/117148
PCT Pub. Date: Jun. 20, 2019

(65) Prior Publication Data
US 2021/0078955 A1     Mar. 18, 2021

(30) Foreign Application Priority Data
Dec. 12, 2017   (JP) .............................. JP2017-238093

(51) Int. Cl.
C07D 239/10     (2006.01)
A61P 3/04       (2006.01)
(Continued)

(52) U.S. Cl.
CPC .......... *C07D 239/10* (2013.01); *A61K 9/0053* (2013.01); *A61P 25/00* (2018.01)

(58) Field of Classification Search
CPC .................................................... C07D 239/10
See application file for complete search history.

(56) References Cited

U.S. PATENT DOCUMENTS 6,596,730 B1   7/2003   Coulton et al.
8,258,163 B2   9/2012   Yanagisawa
(Continued)

FOREIGN PATENT DOCUMENTS

EP   3594202 A1   1/2020
EP   3594203 A1   1/2020
(Continued)

OTHER PUBLICATIONS

Williams et al. (Foye's Principles of Medicinal Chemistry, 5th Edition, pp. 50 and 59-61, 2002, cited in a previous Office Action) (Year: 2002).*

(Continued)

*Primary Examiner* — Marcos L Sznaidman
*Assistant Examiner* — Rayna Rodriguez
(74) *Attorney, Agent, or Firm* — Leydig, Voit & Mayer, Ltd.

(57) ABSTRACT

The present invention aims to provide a novel low-molecular-weight compound showing an orexin receptor agonist activity and expected to be useful as a prophylactic or therapeutic agent for narcolepsy and the like. The present invention provides a compound represented by the formula (I):

(Continued)

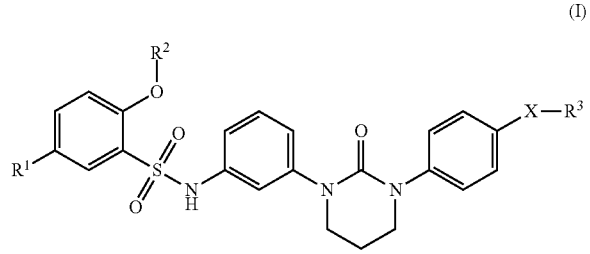

wherein each symbol is as described in the description, or a pharmaceutically acceptable acid addition salt thereof, which has an orexin receptor agonist activity, and an orexin receptor agonist containing the compound or a pharmaceutically acceptable acid addition salt thereof.

16 Claims, 2 Drawing Sheets

(51) Int. Cl.
```
A61P 3/10      (2006.01)
A61P 25/24     (2006.01)
A61P 25/26     (2006.01)
A61P 25/00     (2006.01)
A61K 9/00      (2006.01)
```

(56) References Cited

U.S. PATENT DOCUMENTS

| | | |
|---|---|---|
| 8,871,794 B2 | 10/2014 | Yanagisawa |
| 9,815,787 B2 | 11/2017 | Nagase et al. |
| 10,351,522 B2 | 7/2019 | Nagase et al. |
| 10,428,023 B2 | 10/2019 | Kajita et al. |
| 2016/0362376 A1 | 12/2016 | Nagase et al. |
| 2018/0179151 A1 | 6/2018 | Nagase et al. |

FOREIGN PATENT DOCUMENTS

| | | |
|---|---|---|
| EP | 3663281 A1 | 6/2020 |
| JP | 2002-536447 A | 10/2002 |
| JP | 2015-521999 A | 8/2015 |
| WO | WO 2014/006402 A1 | 1/2014 |
| WO | WO 2014/198880 A1 | 12/2014 |
| WO | WO 2015/088000 A1 | 6/2015 |
| WO | WO 2015/152367 A1 | 10/2015 |
| WO | WO 2016/133160 A1 | 8/2016 |
| WO | WO 2016/199906 A1 | 12/2016 |
| WO | WO 2017/135306 A1 | 8/2017 |
| WO | WO 2018/164191 A1 | 9/2018 |
| WO | WO 2018/164192 A1 | 9/2018 |
| WO | WO 2019/027003 A1 | 2/2019 |

OTHER PUBLICATIONS

Nagahara et al., "Design and Synthesis of Non-Peptide, Selective Orexin Receptor 2 Agonists," *J. Med. Chem.*, 58(20): 7931-7937 (2015).
European Patent Office, Extended European Search Report in European Patent Application No. 18888690.7 (dated May 4, 2021).
Chemelli et al., "Narcolepsy in orexin Knockout Mice: Molecular Genetics of Sleep Regulation," *Cell*, 98(4): 437-451 (1999).
De Lecea et al., "The hypocretins: Hypothalamus-specific peptides with neuroexcitatory activity," *Proc. Natl. Acad. U.S.A.*, 95(1): 322-327 (1998).
Deutschman et al., "Orexinergic Activity Modulates Altered Vital Signs and Pituitary Hormone Secretion in Experimental Sepsis," *Crit. Care Med.*, 41(11): e368-e375 (2013).
Funato et al., "Enhanced Orexin Receptor-2 Signaling Prevents Diet-Induced Obesity and Improves Leptin Sensitivity," *Cell Metab.*, 9(1): 64-76 (2009).
Grossberg et al., "Inflammation-Induced Lethargy Is Mediated by Suppression of Orexin Neuron Activity," *J. Neurosci.*, 31(31): 11376-11386 (2011).
Irukayama-Tomobe et al., "Nonpeptide orexin type-2 receptor agonist ameliorates narcolepsy-cataplexy symptoms in mouse models," *Proc. Natl. Acad. Sci. U.S.A.*, 114(22): 5731-5736 (2017).
Lin et al., "The Sleep Disorder Canine Narcolepsy Is Caused by a Mutation in the Hypocretin (Orexin) Receptor 2 Gene," *Cell*, 98(3): 365-376 (1999).
Mignot et al., "The Role of Cerebrospinal Fluid Hypocretin Measurement in the Diagnosis of Narcolepsy and Other Hypersomnias," *Arch. Neurol.*, 59(10): 1553-1562 (2002).
Moreno et al., "Synthesis and evaluation of new arylsulfonamidomethylcyclohexyl derivatives as human neuropeptide Y $Y_5$ receptor antagonists for the treatment of obesity," *Eur. J. Med. Chem.*, 39(1): 49-58 (2004).
Ogawa et al., "Peripherally administered orexin improves survival of mice with endotoxin shock," *eLIFE*, 5: e21055 (2016).
Sakurai et al., "Orexins and Orexin Receptors: A Family of Hypothalamic Neuropeptides and G Protein-Coupled Receptors that Regulate Feeding Behavior," *Cell*, 92(4): 573-585 (1998).
Toyama et al., "Nonpeptide Orexin-2 Receptor Agonist Attenuates Morphine-induced Sedative Effects in Rats," *Anesthesiology*, 128(5): 992-1003 (2018).
Willie et al., "Distinct Narcolepsy Syndromes in Orexin Receptor-2 and Orexin Null Mice: Molecular Genetic Dissection of Non-REM and REM Sleep Regulatory Processes," *Neuron*, 38(5): 715-730 (2003).
Yamanaka et al., "Hypothalamic Orexin Neurons Regulate Arousal According to Energy Balance in Mice," *Neuron*, 38(5): 701-713 (2003).
Japanese Patent Office, International Preliminary Report on Patentability in International Patent Application No. PCT/JP2018/045523 (dated Jun. 21, 2019).
Japanese Patent Office, International Search Report in International Patent Application No. PCT/JP2018/045523 (dated Feb. 26, 2019).

* cited by examiner

SULFONAMIDE DERIVATIVE OR PHARMACEUTICALLY ACCEPTABLE ACID-ADDITION SALT

CROSS-REFERENCE TO RELATED APPLICATIONS

This patent application is the U.S. national phase of International Patent Application No. PCT/JP2018/045523, filed on Dec. 11, 2018, which claims the benefit of Japanese Patent Application No. 2017-238093 filed on Dec. 12, 2017, which are incorporated by reference in their entireties herein.

TECHNICAL FIELD

The present invention aims to provide a novel compound useful as an excellent orexin receptor agonist.

BACKGROUND ART

Narcolepsy is a sleeping disorder caused by the inability of the brain to control the sleep-wake cycle. The major symptoms of narcolepsy include, for example, excessive daytime sleepiness, cataplexy induced by emotion (particularly strong joy and surprise), hypnagogic hallucination, and hypnagogic paralysis, and narcolepsy patients are under serious influence in general social life. The prevalence of narcolepsy is assumed to be 0.05-0.2% (0.16-0.18% in Japan), and the prevalence indicates that the disease is not rare.

The therapy of narcolepsy mainly includes a drug therapy and life guidance. For drug therapy, methylphenidate, modafinil and pemoline are used to suppress daytime sleepiness, and tricyclic antidepressant, selective serotonin reuptake inhibitor (SSRI), and serotonin and noradrenaline reuptake inhibitor (SNRI) are used to control cataplexy. While these treatment methods are symptomatic therapy of narcolepsy, they are not basic treatment methods.

In recent years, the relationship between narcolepsy and orexin system dysfunction is attracting attention. Orexins are neuropeptides present in the lateral hypothalamic area, which are two kinds of peptide of orexin-A and orexin-B (hypocretin 1, hypocretin 2 (non-patent document 1)). They bind to orexin 1 receptor (hereinafter to be also referred to as OX1R) and orexin 2 receptor (hereinafter to be also referred to as OX2R), which are G-protein coupled receptors (non-patent document 2). It was suggested from model experiments using mouse and dog that lack of orexin receptor (both OX1R and OX2R are expressed), or lack of OX2R causes narcolepsy (non-patent document 3). Furthermore, it was suggested from model experiments using mouse that the function of OX2R is important for maintaining wakefulness (non-patent document 4, non-patent document 5).

On the other hand, many narcolepsy patients were confirmed to show disappearance of orexin nerves, and decreased orexin concentration (non-patent document 6). Therefore, it is strongly suggested that narcolepsy is highly possibly caused by the lack of orexin.

The orexin receptor is widely expressed in the brain. Orexins are peptides, and are not useful for pharmaceutical use since permeability through the blood-brain barrier is extremely low. Therefore, a low-molecular-weight orexin receptor agonist has been desired. In recent years, a compound with a cyclic guanidine skeleton is reported as a small-molecule OX2R agonist (patent document 1).

In addition, orexin system is considered to not only control the above-mentioned sleep-wake but also appropriately control feeding behavior with emotion and energy balance. A mouse under fasting increases the amount of behavior for searching food by increasing the waking time and decreasing the sleep hours. On the other hand, it was clarified that the waking time and the amount of behavior do not increase in orexin receptor-deficient mouse (non-patent document 7). Moreover, it was suggested that an increase of the leptin sensitivity by OX2R regulates the homeostasis of body weight (non-patent document 8). From these findings, an orexin receptor (particularly OX2R) agonist is a potential therapeutic drug for not only narcolepsy but also diabetes, obesity and metabolic syndrome.

Furthermore, it has been reported that sepsis rats show a decrease in the spontaneous activity and a decrease in the activity of the orexin-containing neurons in the perifornical areas of hypothalamus (non-patent document 9). There is a report that intraventricular administration of orexin to a mouse sepsis model led to an increase in the body temperature and recovery of cardiac function (non-patent document 10). From these, it is possible that an orexin receptor agonist may become a therapeutic drug for sepsis.

DOCUMENT LIST

Patent Document patent document 1: U.S. Pat. No. 8,258,163

Non-Patent Documents non-patent document 1: Proc. Natl. Acad. Sci. USA, 95, 322-327 (1998)
non-patent document 2: Cell, 92, 573-585 (1998)
non-patent document 3: Cell, 98, 365-376 (1999)
non-patent document 4: Cell, 98, 437-451 (1999)
non-patent document 5: Neuron, 38, 715-730 (2003)
non-patent document 6: Arch. Neurol., 59, 1553-1562 (2002)
non-patent document 7: Neuron, 38, 701-713 (2003)
non-patent document 8: Cell Metab., 9, 64-76 (2009)
non-patent document 9: J. Neurosci., 31(31), 11376-11386 (2011)
non-patent document 10: Crit. Care Med., 41, 1-8 (2013)

SUMMARY OF THE INVENTION

Problems to be Solved by the Invention

The present invention aims to provide a novel low-molecular-weight compound showing an orexin receptor agonist activity and expected to be useful as an excellent prophylactic or therapeutic agent for narcolepsy and the like.

Means of Solving the Problems

The present inventors have conducted intensive studies in an attempt to solve the aforementioned problems and found a compound represented by the formula (I) mentioned below and having an excellent OX2R agonist activity, which resulted in the completion of the present invention.

That is, the present invention provides the following.

[1] A compound represented by the formula (I):

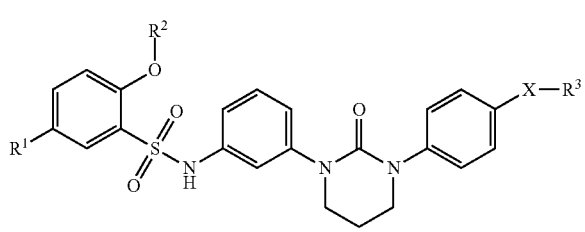

wherein
R$^1$ is
(1) a group represented by the formula (i):

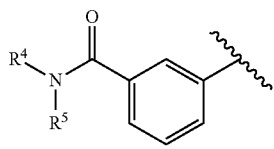

wherein R$^4$ is C$_{1-6}$ alkyl, and R$^5$ is C$_{1-6}$ alkyl,
(2) C$_{1-6}$ alkyl, or
(3) pyrrolidinyl substituted by oxo,
R$^2$ is C$_{1-6}$ alkyl optionally substituted by 1 to 5 atoms selected from a halogen atom and a deuterium atom,
X is a single bond, —O—, —S—, —CH(OH)—, or —C(=O)—, and
R$^3$ is
(2) C$_{2-8}$ alkenyl,
(3) C$_{6-10}$ aryl, or
(4) 5- to 10-membered heteroaryl
wherein C$_{1-8}$ alkyl and C$_{2-8}$ alkenyl are optionally substituted by 1 to 5 halogen atoms,
C$_{6-10}$ aryl and 5- to 10-membered heteroaryl are optionally substituted by optionally selected R$^6$ in the number of 1 to 4, each R$^6$ is independently
a halogen atom,
—NO$_2$,
—OH,
C$_{1-6}$ alkyl,
C$_{1-6}$ haloalkyl,
C$_{1-6}$ alkoxy,
5- to 10-membered heteroaryl,
—NR$^{6a}$R$^{6b}$ wherein R$^{6a}$ is a hydrogen atom, C$_{1-6}$ alkyl or C$_{1-6}$ alkoxy-carbonyl, and R$^{6b}$ is a hydrogen atom or C$_{1-6}$ alkyl,
—C(=O) OR$^{6c}$ wherein R$^{6c}$ is a hydrogen atom or C$_{1-6}$ alkyl,
—C(=O)NR$^{6d}$R$^{6e}$ wherein R$^{6d}$ is a hydrogen atom or C$_{1-6}$ alkyl, and R$^{6e}$ is a hydrogen atom or C$_{1-6}$ alkyl, or
—NH—C(=NR$^{6f}$)—NHR$^{6g}$ wherein R$^{6f}$ is a hydrogen atom or C$_{1-6}$ alkoxy-carbonyl, and R$^{6g}$ is a hydrogen atom or C$_{1-6}$ alkoxy-carbonyl, or R$^6$ in the number of 2 are joined to form methylenedioxy,
or a pharmaceutically acceptable acid addition salt thereof (hereinafter to be also referred to as compound (I)).

[2] The compound of the aforementioned [1], wherein R$^1$ is a group represented by the formula (i):

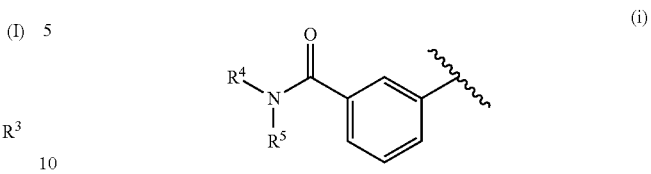

wherein R$^4$ is C$_{1-6}$ alkyl, and R$^5$ is C$_{1-6}$ alkyl, or a pharmaceutically acceptable acid addition salt thereof.

[3] The compound of the aforementioned [1] or [2], wherein R$^2$ is methyl optionally substituted by 1 to 3 atoms selected from a halogen atom and a deuterium atom, or a pharmaceutically acceptable acid addition salt thereof.

[4] The compound of the aforementioned [1] or [2], wherein R$^2$ is methyl, or a pharmaceutically acceptable acid addition salt thereof.

[5] The compound of any one of the aforementioned [1] to [4], wherein X is a single bond or —O—, or a pharmaceutically acceptable acid addition salt thereof.

[6] The compound of any one of the aforementioned [1] to [5], wherein R$^3$ is C$_{1-8}$ alkyl optionally substituted by 1 to 5 halogen atoms, or phenyl, or a pharmaceutically acceptable acid addition salt thereof.

[7] The compound of any one of the aforementioned [1] to [4], wherein X is a single bond, and R$^3$ is C$_{1-8}$ alkyl, or a pharmaceutically acceptable acid addition salt thereof.

[8] A medicament comprising the compound of any one of the aforementioned [1] to [7] or a pharmaceutically acceptable acid addition salt thereof.

[9] An orexin receptor agonist comprising the compound of any one of the aforementioned [1] to [7] or a pharmaceutically acceptable acid addition salt thereof.

[10] An anti-narcolepsy agent comprising the compound of any one of the aforementioned [1] to [7] or a pharmaceutically acceptable acid addition salt thereof.

[11] An agent for improving sleepiness comprising the compound of any one of the aforementioned [1] to [7] or a pharmaceutically acceptable acid addition salt thereof.

[12] A prophylactic or therapeutic agent for obesity, diabetes or depression comprising the compound of any one of the aforementioned [1] to [7] or a pharmaceutically acceptable acid addition salt thereof.

[13] A prophylactic or therapeutic agent for sepsis, severe sepsis or septic shock comprising the compound of any one of the aforementioned [1] to [7] or a pharmaceutically acceptable acid addition salt thereof.

[14] A method of preventing or treating narcolepsy comprising administering an effective amount of the compound of any one of the aforementioned [1] to [7] or a pharmaceutically acceptable acid addition salt thereof.

[15] A method of improving sleepiness comprising administering an effective amount of the compound of any one of the aforementioned [1] to [7] or a pharmaceutically acceptable acid addition salt thereof.

[16] A method of preventing or treating obesity, diabetes or depression comprising administering an effective amount of the compound of any one of the aforementioned [1] to [7] or a pharmaceutically acceptable acid addition salt thereof.

[17] A method of preventing or treating sepsis, severe sepsis or septic shock comprising administering an effective amount of the compound of any one of the aforementioned [1] to [7] or a pharmaceutically acceptable acid addition salt thereof.

[18] The compound of any one of the aforementioned [1] to [7] or a pharmaceutically acceptable acid addition salt thereof for use in the prophylaxis or treatment of narcolepsy.
[19] The compound of any one of the aforementioned [1] to [7] or a pharmaceutically acceptable acid addition salt thereof for use in the improvement of sleepiness.
[20] The compound of any one of the aforementioned [1] to [7] or a pharmaceutically acceptable acid addition salt thereof for use in the prophylaxis or treatment of obesity, diabetes or depression.
[21] The compound of any one of the aforementioned [1] to [7] or a pharmaceutically acceptable acid addition salt thereof for use in the prophylaxis or treatment of sepsis, severe sepsis or septic shock.

Effects of Invention

The compound represented by the formula (I), or a pharmaceutically acceptable acid addition salt thereof of the present invention has an excellent OX2R agonist activity. The compound of the present invention shows OX2R agonist activity by oral administration and prolongs awakening time. Therefore, it can be an orally effective prophylactic or therapeutic agent for narcolepsy, an agent for improving sleepiness, or a prophylactic or therapeutic agent for obesity, diabetes, depression, sepsis, severe sepsis, septic shock or the like.

DESCRIPTION OF EMBODIMENTS

Figure 1:
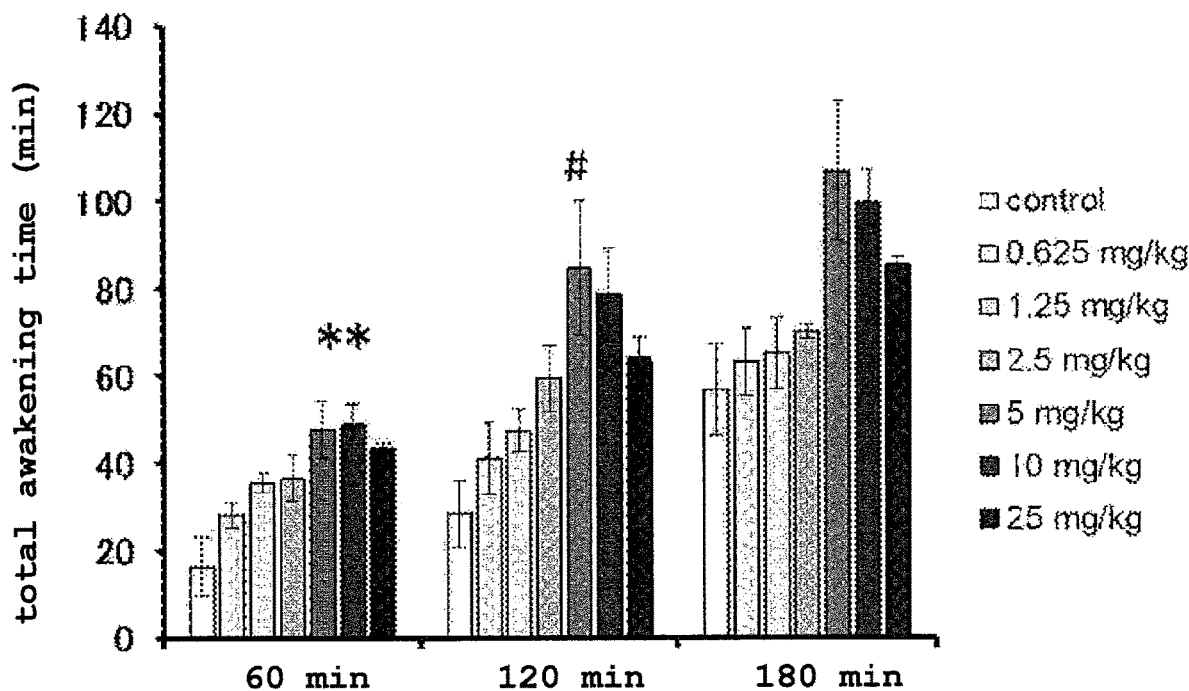
FIG. 1 is a graph showing the results of evaluation (n=3) of the awakening-prolonging effect after oral administration of the test compound (compound of Example 1) in wild-type (WT) mice at 60 min, 120 min, and 180 min after administration. *: p=0.02, #: p=0.052

The following terms used in the present specification are as defined below unless otherwise specified.

The "$C_{1-8}$ alkyl" in the present specification means a monovalent straight chain or branched saturated hydrocarbon group having a carbon number of 1 to 8 and composed of a carbon atom and a hydrogen atom. For example, methyl, ethyl, propyl, isopropyl, butyl, isobutyl, sec-butyl, tert-butyl, pentyl, neopentyl, hexyl, heptyl, octyl and the like can be mentioned. The $C_{1-8}$ alkyl is preferably $C_{1-6}$ alkyl, more preferably $C_{1-4}$ alkyl.

The "$C_{1-6}$ alkyl" in the present specification means a monovalent straight chain or branched saturated hydrocarbon group having a carbon number of 1 to 6 and composed of a carbon atom and a hydrogen atom. For example, methyl, ethyl, propyl, isopropyl, butyl, isobutyl, sec-butyl, tert-butyl, pentyl, neopentyl, hexyl and the like can be mentioned.

The "$C_{1-4}$ alkyl" in the present specification means a monovalent straight chain or branched saturated hydrocarbon group having a carbon number of 1 to 4 and composed of a carbon atom and a hydrogen atom. For example, methyl, ethyl, propyl, isopropyl, butyl, isobutyl, sec-butyl, tert-butyl and the like can be mentioned.

The "$C_{1-6}$ alkoxy" in the present specification means an oxy group to which $C_{1-6}$ alkyl is bonded. For example, methoxy, ethoxy, propoxy, isopropoxy, butoxy, isobutoxy, tert-butoxy and the like can be mentioned.

The "halogen atom" in the present specification means a fluorine atom, a chlorine atom, a bromine atom or an iodine atom.

The "$C_{2-8}$ alkenyl" in the present specification means a monovalent straight chain or branched unsaturated hydrocarbon group having a carbon number of 2 to 8 and at least one double bond, and composed of a carbon atom and a hydrogen atom. For example, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 3-heptenyl, 5-heptenyl, 1-octenyl, 3-octenyl, 5-octenyl and the like can be mentioned. The $C_{2-8}$ alkenyl is preferably $C_{2-6}$ alkenyl, more preferably $C_{2-4}$ alkenyl.

The "$C_{6-10}$ aryl" in the present specification means a monocyclic or fused aromatic carbon cyclic group having 6 to 10 carbon atoms. For example, phenyl, 1-naphthyl, 2-naphthyl and the like can be mentioned.

The "5- to 10-membered heteroaryl" in the present specification means a 5- to 10-membered monocyclic or bicyclic aromatic heterocyclic group containing, as a ring-constituting atom besides carbon atom, 1 to 4 hetero atoms of one or two kinds selected from oxygen atom, sulfur atom and nitrogen atom. For example, thienyl, furyl, pyrrolyl, imidazolyl, pyrazolyl, triazolyl, tetrazolyl, oxazolyl, isoxazolyl, thiazolyl, isothiazolyl, pyridyl, pyridazinyl, pyrimidinyl, furazanyl, pyrazinyl, thiadiazolyl, oxadiazolyl, benzofuryl, benzothienyl, benzimidazolyl, benzothiazolyl, quinolyl, isoquinolyl, cinnolinyl, quinazolinyl, quinoxalinyl, phthalazinyl, 1H-indazolyl and the like can be mentioned.

The "$C_{1-6}$ haloalkyl" in the present specification means a $C_{1-6}$ alkyl substituted by 1 to 5 (preferably 1 to 3) halogen atoms. For example, trifluoromethyl, 2,2,2-trifluoroethyl, 3,3,3-trifluoropropyl and the like can be mentioned. It is preferably trifluoromethyl.

The "$C_{1-6}$ alkoxy-carbonyl" in the present specification means a carbonyl group bonded to $C_{1-6}$ alkoxy. For example, methoxycarbonyl, ethoxycarbonyl, propoxycarbonyl, isopropoxycarbonyl, butoxycarbonyl, isobutoxycarbonyl, tert-butoxycarbonyl and the like can be mentioned.

The "pyrrolidinyl substituted by oxo" in the present specification means pyrrolidinyl substituted by one oxo group. For example, 5-oxopyrrolidin-3-yl and the like can be mentioned.

The "anti-narcolepsy agent" in the present specification means an agent for the prophylaxis or treatment of narcolepsy.

The "agent for improving sleepiness" in the present specification means a medicament for improving daytime sleepiness due to shift work, jet lag, insomnia, sleep apnea syndrome and the like.

The definition of each symbol in the formulas and preferred embodiments of the present invention are explained in the following.

R$^1$ is
(1) a group represented by the formula (i):

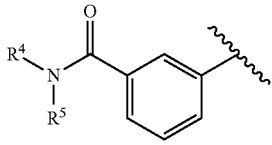

wherein R$^4$ is C$_{1-6}$ alkyl, and R$^5$ is C$_{1-6}$ alkyl,
(2) C$_{1-6}$ alkyl, or
(3) pyrrolidinyl substituted by oxo.

R$^1$ is preferably a group represented by the formula (i):

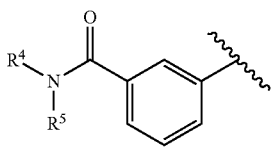

wherein R$^4$ is C$_{1-6}$ alkyl (e.g., methyl), and R$^5$ is C$_{1-6}$ alkyl (e.g., methyl), more preferably, 3-(dimethylcarbamoyl)phenyl.

In another embodiment, R$^1$ is preferably C$_{1-6}$ alkyl (e.g., isopropyl).

In still another embodiment, R$^1$ is preferably pyrrolidinyl substituted by oxo (e.g., 5-oxopyrrolidin-3-yl).

R$^2$ is C$_{1-6}$ alkyl optionally substituted by 1 to 5 atoms selected from a halogen atom and a deuterium atom.

Examples of R$^2$ include methyl, trifluoromethyl, trideuteriomethyl and the like.

R$^2$ is preferably C$_{1-6}$ alkyl (e.g., methyl) optionally substituted by 1 to 3 atoms selected from a halogen atom (e.g., fluorine atom) and a deuterium atom.

R$^2$ is more preferably C$_{1-4}$ alkyl (e.g., methyl) optionally substituted by 1 to 3 deuterium atoms, particularly preferably methyl or trideuteriomethyl.

X is a single bond, —O—, —S—, —CH(OH)—, or —C(=O)—.

X is preferably a single bond or —O—, more preferably a single bond.

R$^3$ is
(1) C$_{1-8}$ alkyl,
(2) C$_{2-8}$ alkenyl,
(3) C$_{6-10}$ aryl, or
(4) 5- to 10-membered heteroaryl wherein C$_{1-8}$ alkyl and C$_{2-8}$ alkenyl are optionally substituted by 1 to 5 halogen atoms, C$_{6-10}$ aryl and 5- to 10-membered heteroaryl are optionally substituted by R$^6$ in the number of 1 to 4 which are selected optionally,
each R$^6$ is independently
a halogen atom,
—NO$_2$,
—OH,
C$_{1-6}$ alkyl,
C$_{1-6}$ haloalkyl,
C$_{1-6}$ alkoxy,
5- to 10-membered heteroaryl,
—NR$^{6a}$R$^{6b}$ wherein R$^{6a}$ is a hydrogen atom, C$_{1-6}$ alkyl or C$_{1-6}$ alkoxy-carbonyl, and R$^{6b}$ is a hydrogen atom or C$_{1-6}$ alkyl,
—C(=O)OR$^{6c}$ wherein R$^{6c}$ is a hydrogen atom or C$_{1-6}$ alkyl,
—C(=O)NR$^{6d}$R$^{6e}$ wherein R$^{6d}$ is a hydrogen atom or C$_{1-6}$ alkyl, and R$^{6e}$ is a hydrogen atom or C$_{1-6}$ alkyl, or
—NH—C(=NR$^{6f}$)—NHR$^{6g}$ wherein R$^{6f}$ is a hydrogen atom or C$_{1-6}$ alkoxy-carbonyl, and R$^{6g}$ is a hydrogen atom or C$_{1-6}$ alkoxy-carbonyl, or R$^6$ in the number of 2 are joined to form methylenedioxy.

The C$_{1-8}$ alkyl for R$^3$ is preferably C$_{1-6}$ alkyl, more preferably C$_{1-4}$ alkyl.

R$^3$ is preferably C$_{1-8}$ alkyl optionally substituted by 1 to 5 halogen atoms (e.g., fluorine atom) (e.g., methyl, ethyl, propyl, isopropyl, butyl, isobutyl, octyl, trifluoromethyl, 2,2,2-trifluoroethyl), or C$_{6-10}$ aryl (e.g., phenyl),
more preferably C$_{1-6}$ alkyl optionally substituted by 1 to 5 halogen atoms (e.g., fluorine atom) (e.g., methyl, ethyl, propyl, isopropyl, butyl, isobutyl, trifluoromethyl, 2,2,2-trifluoroethyl), or C$_{6-10}$ aryl (e.g., phenyl),
further preferably C$_{1-4}$ alkyl (e.g., methyl, ethyl, propyl, butyl, isobutyl),
particularly preferably propyl.

In a preferred embodiment, X is a single bond, and R$^3$ is C$_{1-6}$ alkyl (preferably C$_{1-4}$ alkyl (e.g., methyl, ethyl, propyl, isopropyl, butyl)).

Preferable examples of the compound represented by the above-mentioned formula (I) in the present invention include the following compounds.

A compound represented by the formula (I-A):

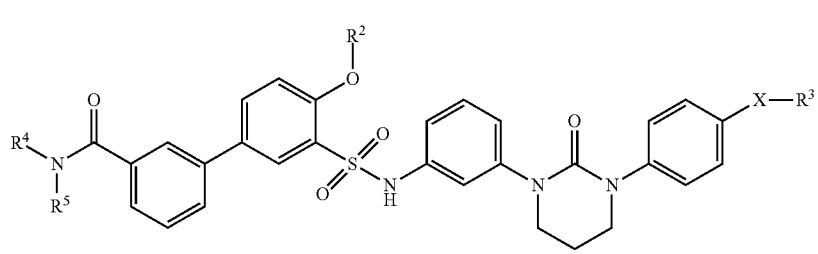

wherein each symbol is as defined in the aforementioned [1], or a pharmaceutically acceptable acid addition salt thereof.

In the formula (I-A), preferred embodiments of R$^2$, X, R$^3$, R$^4$, and R$^5$ are as follows.

R$^2$ is preferably C$_{1-6}$ alkyl (e.g., methyl) optionally substituted by 1 to 3 atoms selected from a halogen atom (e.g., fluorine atom) and a deuterium atom.

R$^2$ is more preferably C$_{1-4}$ alkyl (e.g., methyl) optionally substituted by 1 to 3 deuterium atoms, particularly preferably methyl or trideuteriomethyl.

X is preferably a single bond or —O—, more preferably a single bond.

$R^3$ is preferably $C_{1-8}$ alkyl optionally substituted by 1 to 5 halogen atoms (e.g., fluorine atom) (e.g., methyl, ethyl, propyl, isopropyl, butyl, isobutyl, octyl, trifluoromethyl, 2,2,2-trifluoroethyl), or $C_{6-10}$ aryl (e.g., phenyl), more preferably $C_{1-6}$ alkyl optionally substituted by 1 to 5 halogen atoms (e.g., fluorine atom) (e.g., methyl, ethyl, propyl, isopropyl, butyl, isobutyl, trifluoromethyl, 2,2,2-trifluoroethyl), or $C_{6-10}$ aryl (e.g., phenyl), further preferably $C_{1-4}$ alkyl (e.g., methyl, ethyl, propyl, butyl, isobutyl), particularly preferably propyl.

In a preferred embodiment, X is a single bond, and $R^3$ is $C_{1-6}$ alkyl (preferably $C_{1-4}$ alkyl (e.g., methyl, ethyl, propyl, isopropyl, butyl)).

$R^4$ is preferably $C_{1-4}$ alkyl (e.g., methyl), and $R^5$ is preferably $C_{1-4}$ alkyl (e.g., methyl).

[Compound I-1]

A compound of the formula (I), wherein

X is a single bond or —O—, and $R^3$ is $C_{1-8}$ alkyl optionally substituted by 1 to 5 halogen atoms, or phenyl, or a pharmaceutically acceptable acid addition salt thereof.

[Compound I-2]

A compound of the formula (I), wherein

X is a single bond, $R^2$ is $C_{1-4}$ alkyl optionally substituted by 1 to 3 deuterium atoms (e.g., methyl, trideuteriomethyl), and $R^3$ is $C_{1-4}$ alkyl (e.g., methyl, ethyl, propyl, isopropyl, butyl), or a pharmaceutically acceptable acid addition salt thereof.

[Compound I-A1]

A compound of the formula (I-A), wherein

X is a single bond or —O—, and $R^3$ is $C_{1-8}$ alkyl optionally substituted by 1 to 5 halogen atoms, or phenyl, or a pharmaceutically acceptable acid addition salt thereof.

[Compound I-A2]

A compound of the formula (I-A), wherein

X is a single bond, $R^2$ is $C_{1-4}$ alkyl optionally substituted by 1 to 3 deuterium atoms (e.g., methyl, trideuteriomethyl), and $R^3$ is $C_{1-4}$ alkyl (e.g., methyl, ethyl, propyl, isopropyl, butyl), or a pharmaceutically acceptable acid addition salt thereof.

As a specific example of the compound represented by the formula (I),

4'-methoxy-N,N-dimethyl-3'-(N-(3-(2-oxo-3-(4-propylphenyl)tetrahydropyrimidin-1(2H)-yl)phenyl)sulfamoyl)-[1,1'-biphenyl]-3-carboxamide, or 4'-(methoxy-d3)-N,N-dimethyl-3'-(N-(3-(2-oxo-3-(4-propylphenyl)tetrahydropyrimidin-1(2H)-yl)phenyl)sulfamoyl)-[1,1'-biphenyl]-3-carboxamide, or a pharmaceutically acceptable acid addition salt thereof is preferable, and 4'-methoxy-N,N-dimethyl-3'-(N-(3-(2-oxo-3-(4-propylphenyl)tetrahydropyrimidin-1(2H)-yl)phenyl)sulfamoyl)-[1,1'-biphenyl]-3-carboxamide, or a pharmaceutically acceptable acid addition salt thereof is particularly preferable.

As a pharmaceutically acceptable acid addition salt of the compound of the formula (I) of the present invention, inorganic acid salts such as hydrochloride, sulfate, nitrate, hydrobromide, hydroiodide, phosphate and the like, organic carbonates such as acetate, lactate, citrate, oxalate, glutarate, malate, tartrate, fumarate, mandelate, maleate, benzoate, phthalate and the like, organic sulfonates such as methanesulfonate, ethanesulfonate, benzenesulfonate, p-toluenesulfonate, camphorsulfonate and the like, and the like can be mentioned; however, these are not limitative. Of these, hydrochloride, hydrobromide, phosphate, tartrate, methanesulfonate or camphorsulfonate is preferable, and hydrochloride, tartrate or methanesulfonate is further preferably used and hydrochloride is particularly preferably used; however, these are also not limitative.

The compound of the above-mentioned formula (I) of the present invention can be produced by an appropriate method based on the characteristics derived from the basic skeleton and substituents thereof. While the starting materials and reagents to be used for the production of these compounds are generally available or can be synthesized by a method known to those of ordinary skill in the art, which follows the procedures described in reference documents such as Organic Reactions (Wiley&Sons), Fieser and Fieser's Reagent for Organic Synthesis (Wiley&Sons) and the like.

As a specific production method of the compound of the above-mentioned formula (I) of the present invention, for example, the method shown in Scheme 1 can be mentioned.

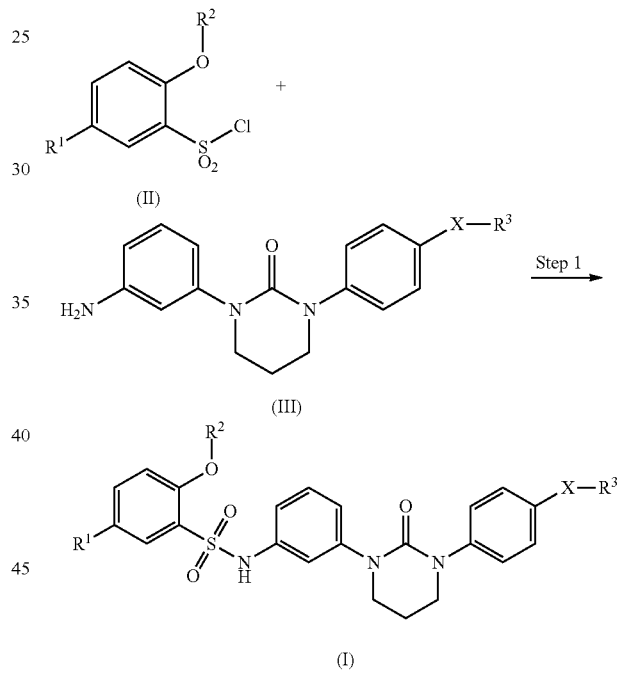

Scheme 1 wherein $R^1$, $R^2$, X and $R^3$ are as defined above.

Step 1

Compound (I) can be obtained by, for example, amidating sulfonyl chloride compound (II) with amine compound (III).

As the solvent, halogenated hydrocarbon solvents such as dichloromethane, chloroform, 1,2-dichloroethane and the like, ether solvents such as diethyl ether, tetrahydrofuran (THF), 1,2-dimethoxyethane (DME), dioxane and the like, aprotic polar solvents such as N,N-dimethylformamide (DMF), dimethyl sulfoxide (DMSO) and the like, pyridine, or a mixed solvent thereof can be used. Generally, pyridine, dichloromethane or THF is preferably used. The sulfonyl chloride compound (II) is used in an amount of 0.5-20 equivalents, preferably 1.0-10 equivalents, relative to amine compound (III).

Examples of the base include sodium carbonate, potassium carbonate, cesium carbonate, potassium phosphate, sodium hydroxide, potassium hydroxide, barium hydroxide, triethylamine, diisopropylethylamine, pyridine, 4-dimethylaminopyridine and the like, and diisopropylethylamine, triethylamine or pyridine is preferably used. When pyridine is used as a base, pyridine can also be used as a reaction solvent.

The reaction temperature is generally −40 to 150° C., preferably 0 to 80° C. While the reaction time is appropriately selected according to the conditions such as reaction temperature and the like, it is generally about 10 min to 48 hr. While the concentration of substrate (II) in the reaction system is not particularly limited, it is generally preferably 0.001 mmol/L to 1 mol/L.

The sulfonyl chloride compound (II) and amine compound (III) can be produced by the method described in the following Production Examples, or a method similar thereto.

An orexin receptor agonist (orexin 2 receptor agonist) containing the compound of the present invention is effective for not only human but also mammals other than human, for example, mouse, rat, hamster, rabbit, cat, dog, bovine, sheep, monkey and the like.

Also, the compound of the present invention is used not only as an agent for the prophylaxis or treatment of narcolepsy as mentioned above but also can be used in a method of preventing or treating narcolepsy, or for the production of a medicament for the prophylaxis or treatment of narcolepsy.

Furthermore, the compound of the present invention can also be used as an agent for improving sleepiness, or a prophylactic or therapeutic agent for obesity, diabetes, depression, sepsis, severe sepsis, septic shock and the like.

When the compound of the present invention is clinically used as an agent for the prophylaxis or treatment of narcolepsy, an agent for improving sleepiness or a prophylactic or therapeutic agent for obesity, diabetes, depression, sepsis, severe sepsis, septic shock and the like, the medicament may be a free form of the compound of the present invention or an acid addition salt thereof, or additives such as excipient, stabilizer, preservative, buffering agent, solubilizing agent, emulsifier, diluent, isotonicity agent and the like may be mixed as appropriate. Examples of the administration form include oral preparations such as tablet, capsule, granule, powder, syrup and the like, parenteral agents such as injection, suppository, liquid and the like, topical administration of ointment, cream, adhesive preparation and the like, and the like.

The agent for the prophylaxis or treatment of narcolepsy, the agent for improving sleepiness, or the prophylactic or therapeutic agent for obesity, diabetes, depression, sepsis, severe sepsis, septic shock and the like of the present invention desirably contains 0.001-90 wt %, preferably 0.01-70 wt %, of the above-mentioned active ingredient. The amount thereof to be used is appropriately determined according to the symptom, age, body weight, and administration method. In the case of injection for an adult, the amount of the active ingredient is 0.1 μg-1 g per day, 1 μg-1 g in the case of an oral preparation, and 1 μg-10 g in the case of an adhesive preparation, each of which can be administered in one to several portions.

In addition, the agent for the prophylaxis or treatment of narcolepsy or the agent for improving sleepiness of the present invention can also be used in combination with an agent for the prophylaxis or treatment of strong sleepiness and dozing during the day, an agent for the prophylaxis or treatment of deep sleep disorder, or an agent for the prophylaxis or treatment of cataplexy.

As an agent for the prophylaxis or treatment of strong sleepiness and dozing during the day, central nervous system stimulants such as methylphenidate, pemoline, modafinil and the like, and the like can be mentioned.

As an agent for the prophylaxis or treatment of deep sleep disorder, sleeping drugs such as triazolam, vegetamin B and the like, antianxiety drug and the like can be mentioned.

As an agent for the prophylaxis or treatment of cataplexy, tricyclic antidepressants such as clomipramine hydrochloride, brotizolam, imipramine hydrochloride and the like, selective serotonin reuptake inhibitors (SSRI) such as fluvoxamine maleate, paroxetine, hydrochloride and the like, serotonin and noradrenaline reuptake inhibitors (SNRI) such as milnacipran hydrochloride, duloxetine hydrochloride and the like, and the like can be mentioned.

EXAMPLES

The present invention is specifically explained in the following by referring to Examples. In the following Examples, the following abbreviations are used.

DBU: 1,8-diazabicyclo[5.4.0]-7-undecene
DME: 1,2-dimethoxyethane
DMF: N,N-dimethylformamide
Et: ethyl
iBu: isobutyl
iPr: isopropyl
Me: methyl
nPr: normal propyl
nBu: normal butyl
nOct: normal octyl
Ph: phenyl
Tf: trifluoromethanesulfonyl
THF: tetrahydrofuran The compound names were determined using ChemBioDraw Ultra ver. 12.0.3 of Cambridge Corporation.

The "room temperature" in the following Examples and Production Examples mean generally from about 10° C. to about 35° C. Unless particularly indicated, % shows weight percent.

Production Example (1)

-continued

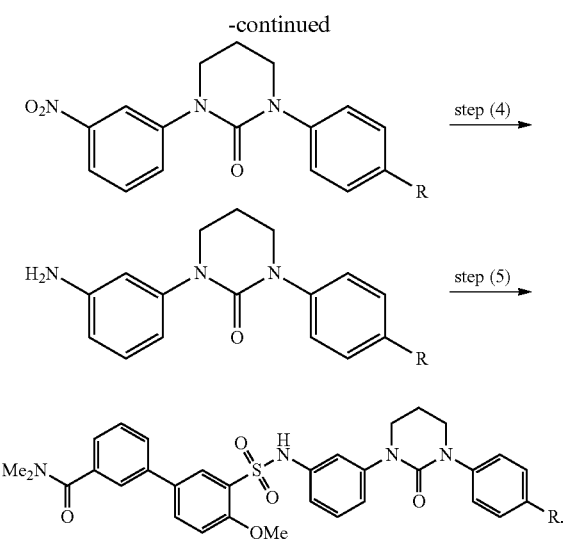

(1) 3'-(dimethylcarbamoyl)-4-methoxy-[1,1'-biphenyl]-3-sulfonyl Chloride

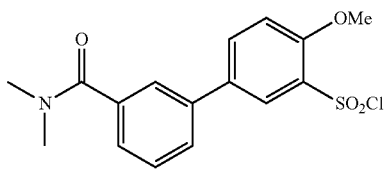 [SMILES: COc1ccc(-c2cccc(C(=O)N(C)C)c2)cc1S(=O)(=O)Cl]

(i) Under an argon atmosphere, to a solution of 4-bromoanisole (1.0 mL) in DME (20.0 mL) were added 3-(N,N-dimethylaminocarbonyl)phenylboronic acid (1.60 g), sodium carbonate (1.80 g), water (2.0 mL) and tetrakis(triphenylphosphine)palladium (250.0 mg), and the mixture was heated under reflux overnight. The reaction mixture was filtered through Celite, and the filtrate was concentrated. To the obtained residue was added pure water and the mixture was extracted with chloroform. The organic layer was dried over sodium sulfate and filtered, and the filtrate was concentrated under reduced pressure. The obtained residue was purified by silica gel column chromatography (eluent: ethyl acetate/hexane=1/2→1/1) to give 4'-methoxy-N,N-dimethyl-[1,1'-biphenyl]-3-carboxamide (1.72 g).

(ii) Under an argon atmosphere, to chlorosulfonic acid (870 μL) was slowly added a solution of 4'-methoxy-N,N-dimethyl-[1,1'-biphenyl]-3-carboxamide (1.10 g) in dichloromethane (4.0 mL), and the mixture was stirred under ice-cooling for 10 min. The reaction mixture was warmed to room temperature and stirred for 2 hr. Thionyl chloride (950 μL) and DMF (1.70 mL) were added, and the mixture was stirred at room temperature overnight. The reaction mixture was poured into ice and the mixture was stirred for 1 hr and extracted with chloroform. The organic layer was dried over sodium sulfate and filtered, and the filtrate was concentrated under reduced pressure. The obtained residue was purified by silica gel column chromatography (eluent: ethyl acetate/hexane=50% to 100%) to give 3'-(dimethylcarbamoyl)-4-methoxy-[1,1'-biphenyl]-3-sulfonyl chloride (1.40 g).

(2) 1-(3-nitrophenyl)tetrahydropyrimidin-2(1H)-one

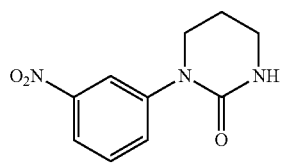 [SMILES: O=C1NCCCN1c1cccc([N+](=O)[O-])c1]

(i) Under an argon atmosphere, to 3-fluoronitrobenzene (1.50 mL) was added 1,3-propanediamine (17.7 mL), and the mixture was stirred at 110° C. for 11 hr. To the reaction mixture was added water, and the mixture was extracted with chloroform. The organic layer was dried over sodium sulfate and filtered, and the filtrate was concentrated.

(ii) To a solution of the obtained residue in dry THF (45 mL) was added under ice-cooling 1,1-carbonyldiimidazole (3.20 g), and the mixture was stirred for 1.5 hr. To the reaction mixture was added saturated brine, and the mixture was extracted with ethyl acetate. The organic layer was dried over magnesium sulfate and filtered, and the filtrate was concentrated. The obtained residue was purified by silica gel column chromatography (eluent: methanol/chloroform=5% to 7%) to give 1-(3-nitrophenyl)tetrahydropyrimidin-2(1H)-one (2.31 g).

(3) 1-(3-nitrophenyl)-3-(4-propylphenyl)tetrahydropyrimidin-2(1H)-one

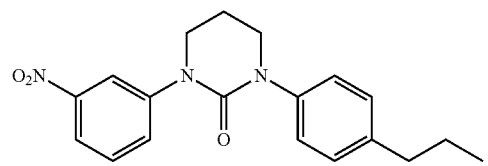 [SMILES: CCCc1ccc(N2CCCN(c3cccc([N+](=O)[O-])c3)C2=O)cc1]

Under an argon atmosphere, to a solution of 1-(3-nitrophenyl)tetrahydropyrimidin-2(1H)-one (150 mg) in anhydrous toluene (680 μL) were added copper iodide (95.0 mg), N,N'-dimethylcyclohexane-1,2-diamine (142 mg), anhydrous potassium carbonate (234 mg) and 1-bromo-4-propylbenzene (147 μL), and the mixture was stirred under heating under reflux for 48 hr. The reaction mixture was allowed to cool, chloroform was added, and the mixture was filtered through Celite and washed with chloroform. The filtrate was washed with distilled water and saturated brine, dried over magnesium sulfate and filtered, and the filtrate was concentrated under reduced pressure. The obtained residue was purified by silica gel column chromatography (eluent: methanol/chloroform=5%) to give 1-(3-nitrophenyl)-3-(4-propylphenyl)tetrahydropyrimidin-2(1H)-one (212 mg).

(4) 1-(3-aminophenyl)-3-(4-propylphenyl)tetrahydropyrimidin-2(1H)-one

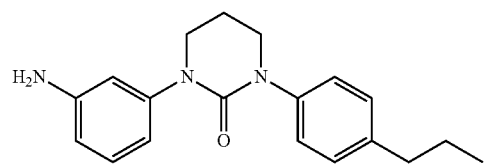

To a solution of 1-(3-nitrophenyl)-3-(4-propylphenyl)tetrahydropyrimidin-2(1H)-one (146 mg) in ethanol (20.0 mL) was added 5% palladium-activated carbon (47.5 mg), and the mixture was stirred under a hydrogen atmosphere at room temperature for 1 hr. The reaction mixture was allowed to cool and filtered through Celite, and the filtrate was concentrated. The obtained residue was purified by silica gel column chromatography (eluent: methanol/chloroform=5%) to give 1-(3-aminophenyl)-3-(4-propylphenyl)tetrahydropyrimidin-2(1H)-one (135 mg).

(5) 4'-methoxy-N,N-dimethyl-3'-(N-(3-(2-oxo-3-(4-propylphenyl)tetrahydropyrimidin-1(2H)-yl)phenyl)sulfamoyl)-[1,1'-biphenyl]-3-carboxamide

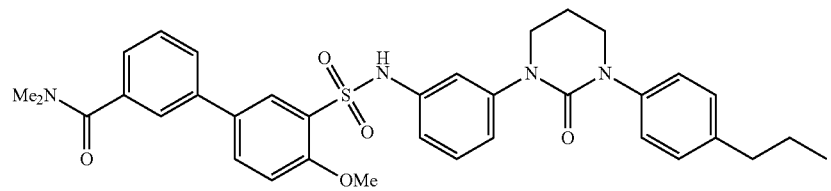 [SMILES: CCCc1ccc(N2CCCN(c3cccc(NS(=O)(=O)c4cc(-c5cccc(C(=O)N(C)C)c5)ccc4OC)c3)C2=O)cc1]

Under an argon atmosphere, to a solution of 1-(3-aminophenyl)-3-(4-propylphenyl)tetrahydropyrimidin-2(1H)-one (23.3 mg) in anhydrous pyridine (1.50 mL) was added 3'-(dimethylcarbamoyl)-4-methoxy-[1,1'-biphenyl]-3-sulfonyl chloride (27.7 mg), and the mixture was stirred at room temperature for 1 hr. To the reaction mixture was added distilled water, and the mixture was extracted with chloroform. The organic layer was washed with saturated brine, dried over magnesium sulfate and filtered, and the filtrate was concentrated under reduced pressure. The obtained residue was dissolved in chloroform, and the solution was added to ice-cooled hexane by small portions. The resulting precipitate was filtered to give 4'-methoxy-N,N-dimethyl-3'-(N-(3-(2-oxo-3-(4-propylphenyl)tetrahydropyrimidin-1(2H)-yl)phenyl)sulfamoyl)-[1,1'-biphenyl]-3-carboxamide (35.4 mg).

The compounds (Examples 2-5) described in the following Table 1 were also synthesized similarly from bromobenzene having the corresponding R group.

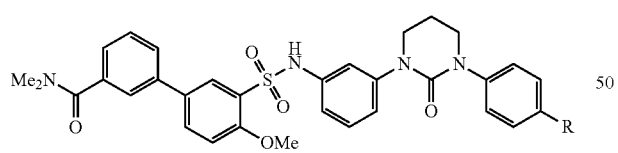

TABLE 1

| Ex. No. | R | $^1$H-NMR |
|---|---|---|
| 1 | nPr | 1H NMR (400 MHz, CDCl3) δ 0.93 (t, J = 7.3 Hz, 4H), 1.62 (q, J = 7.7 Hz, 3H), 2.21 (p, J = 6.0 Hz, 2H), 2.55 (t, J = 7.3, 6.3 Hz, 2H), 2.99 (s, 3H), 3.13 (s, 3H), 3.67-3.81 (m, 4H), 4.06 (s, 3H), 6.79-6.86 (m, 1H), 6.90 (s, 1H), 7.08 (d, J = 8.7 Hz, 1H), 7.10-7.16 (m, 5H), 7.19 (d, J = 8.6 Hz, 2H), 7.35 (dt, J = 7.8, 1.5 Hz, 1H), 7.37-7.44 (m, 1H), 7.52-7.57 (m, 2H), 7.71 (dd, J = 8.6, 2.4 Hz, 1H), 8.06 (d, J = 2.4 Hz, 1H). |
| 2 | Me | 1H NMR (400 MHz, CDCl3) δ 2.17 (p, J = 5.9 Hz, 2H), 2.29 (s, 3H), 2.98 (s, 3H), 3.12 (s, 3H), 3.67 (t, J = 5.7 Hz, 2H), 3.72 (t, J = 5.9 Hz, 2H), 3.94 (s, 3H), 6.77-6.86 (m, 1H), 6.99-7.14 (m, 6H), 7.17 (d, J = 8.4 Hz, 2H), 7.33 (d, J = 7.5 Hz, 1H), 7.39 (t, J = 7.9 Hz, 1H), 7.45 (s, 1H), 7.49-7.56 (m, 2H), 7.66 (dd, J = 8.7, 2.3 Hz, 1H), 8.05 (d, J = 2.3 Hz, 1H). |
| 3 | Et | 1H NMR (400 MHz, CDCl3) δ 1.21 (t, J = 7.6 Hz, 3H), 2.20 (p, J = 5.9 Hz, 2H), 2.62 (q, J = 7.6 Hz, 2H), 2.99 (s, 3H), 3.12 (s, 3H), 3.68-3.78 (m, 4H), 4.04 (s, 3H), 6.80-6.86 (m, 1H), 6.99 (s, 1H), 7.07 (d, J = 8.7 Hz, 1H), 7.10-7.17 (m, 5H), 7.20 (d, J = 8.7 Hz, 2H), 7.34 (dt, J = 7.6, 1.4 Hz, 1H), 7.37-7.44 (m, 1H), 7.51-7.56 (m, 2H), 7.70 (dd, J = 8.6, 2.4 Hz, 1H), 8.05 (d, J = 2.4 Hz, 1H). |
| 4 | iPr | 1H NMR (400 MHz, CDCl3) δ 1.23 (d, J = 6.9 Hz, 6H), 2.20 (p, J = 6.2 Hz, 2H), 2.88 (p, J = 6.9 Hz, 1H). 2.99 (s, 3H), 3.12 (s, 3H), 3.74 (dt, J = 11.8, 5.9 Hz, 4H), 4.05 (s, 3H), 6.80-6.85 (m, 1H), 6.94 (s, 1H), 7.08 (d, J = 8.7 Hz, 1H), 7.10-7.16 (m, 3H), 7.16-7.22 (m, 4H), 7.32-7.36 (m, 1H), 7.40 (td, J = 7.6, 1.1 Hz, 1H), 7.52-7.57 (m, 2H), 7.70 (dd, J = 8.6, 2.4 Hz, 1H), 8.05 (d, J = 2.4 Hz, 1H). |
| 5 | OMe | 1H NMR (400 MHz, CDCl3) δ 2.20 (p, J = 6.0 Hz, 2H), 2.99 (s, 3H), 3.13 (s, 3H), 3.71-3.73 (m, 4H), 3.78 (s, 3H), 4.02 (s, 3H), 6.81-6.83 (m, 1H), 6.85 (d, J = 9.0 Hz, 2H), 7.05-7.14 (m, 5H), 7.20 (d, J = 9.0 Hz, 2H), 7.35 (ddd, J = 7.2, 1.2, 1.2 Hz, 1H), 7.39-7.43 (m, 1H), 7.53-7.56 (m, 2H), 7.70 (dd, J = 8.8, 2.4 Hz, 1H), 8.06 (d, J = 2.4 Hz, 1H). |

Production Example (2)

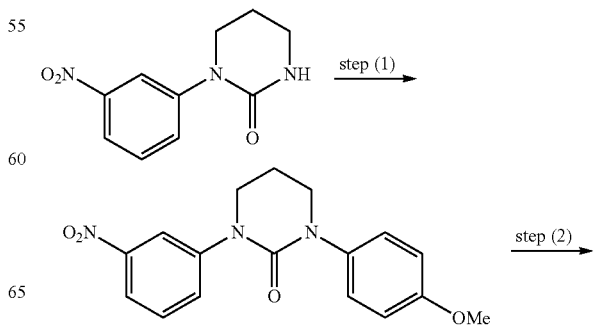

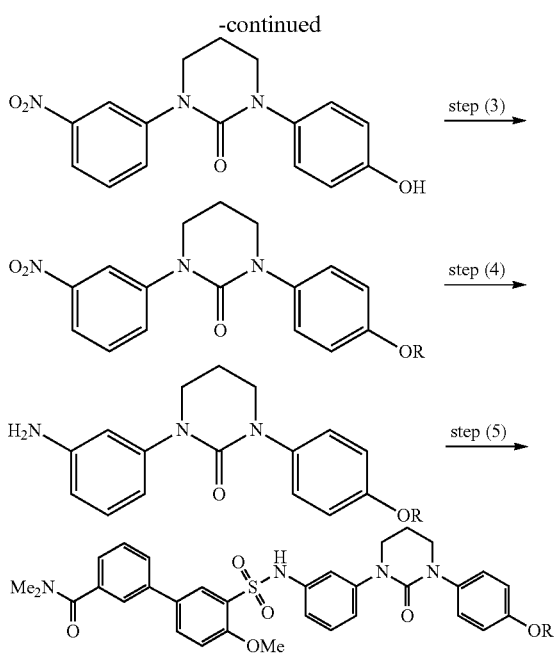

(1) 1-(4-methoxyphenyl)-3-(3-nitrophenyl)tetrahydropyrimidin-2(1H)-one

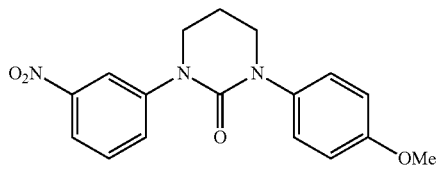 [SMILES: COc1ccc(N2CCCN(c3cccc([N+](=O)[O-])c3)C2=O)cc1]

Under an argon atmosphere, to a solution of 1-(3-nitrophenyl)tetrahydropyrimidin-2(1H)-one (221 mg) in anhydrous toluene (2.0 mL) were added copper iodide (114 mg), N,N'-dimethylcyclohexane-1,2-diamine (187 μL), anhydrous potassium carbonate (345 mg) and 4-iodoanisole (351 mg), and the mixture was stirred under heating under reflux for 24 hr. The reaction mixture was allowed to cool, chloroform was added, and the mixture was filtered through Celite and washed with chloroform. The filtrate was washed with distilled water and saturated brine, dried over sodium sulfate and filtered, and the filtrate was concentrated under reduced pressure. The obtained residue was purified by silica gel column chromatography (eluent: methanol/chloroform=5%) to give 1-(4-methoxyphenyl)-3-(3-nitrophenyl)tetrahydropyrimidin-2(1H)-one (323 mg).

(2) 1-(4-hydroxyphenyl)-3-(3-nitrophenyl)tetrahydropyrimidin-2(1H)-one

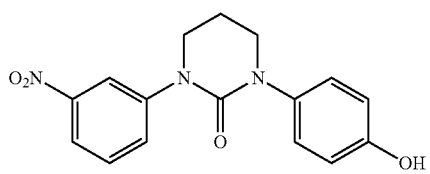 [SMILES: O=C1N(c2ccc(O)cc2)CCCN1c1cccc([N+](=O)[O-])c1]

Under an argon atmosphere, to a suspension of 1-(4-methoxyphenyl)-3-(3-nitrophenyl)tetrahydropyrimidin-2(1H)-one (314 mg) in dichloromethane (2.0 mL) was added 1 M boron tribromide dichloromethane solution (7.20 mL) under ice-cooling, and the mixture was stirred for 2 hr. To the reaction mixture was added aqueous ammonia, and the mixture was extracted with chloroform. The organic layer was washed with saturated brine, dried over sodium sulfate and filtered, and the filtrate was concentrated under reduced pressure. The obtained residue was purified by silica gel column chromatography (eluent: methanol/chloroform=5%) to give 1-(4-hydroxyphenyl)-3-(3-nitrophenyl)tetrahydropyrimidin-2(1H)-one (169 mg).

(3) 1-(4-ethoxyphenyl)-3-(3-nitrophenyl)tetrahydropyrimidin-2(1H)-one

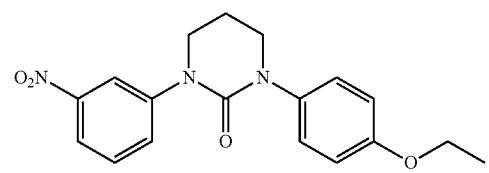 [SMILES: CCOc1ccc(N2CCCN(c3cccc([N+](=O)[O-])c3)C2=O)cc1]

Under an argon atmosphere, to a solution of 1-(4-hydroxyphenyl)-3-(3-nitrophenyl)tetrahydropyrimidin-2(1H)-one (114.5 mg) in DMF (2.0 mL) were added potassium carbonate (101.0 mg) and ethyl iodide (32.2 μL), and the mixture was stirred at 60° C. for 5 hr. To the reaction mixture was further added ethyl iodide (128 μL), and the mixture was stirred for 12 hr. To the reaction mixture was added pure water, and the mixture was extracted with chloroform. The organic layer was dried over sodium sulfate and filtered, and the filtrate was concentrated. The obtained residue was purified by silica gel column chromatography (eluent: ethyl acetate/hexane=50%) to give 1-(4-ethoxyphenyl)-3-(3-nitrophenyl)tetrahydropyrimidin-2(1H)-one (116 mg).

(4) 1-(3-aminophenyl)-3-(4-ethoxyphenyl)tetrahydropyrimidin-2(1H)-one

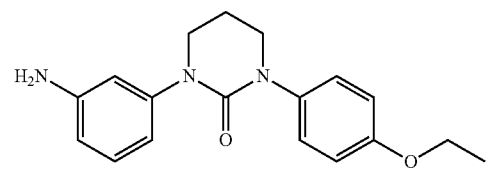

To a solution of 1-(4-ethoxyphenyl)-3-(3-nitrophenyl)tetrahydropyrimidin-2(1H)-one (112 mg) in ethanol (20.0 mL) was added 5% palladium-activated carbon (114 mg), and the mixture was stirred under a hydrogen atmosphere at room temperature for 4 hr. The reaction mixture was allowed to cool and filtered through Celite, and the filtrate was concentrated. The obtained residue was purified by silica gel column chromatography (eluent: methanol/chloroform=5%) to give 1-(3-aminophenyl)-3-(4-ethoxyphenyl)tetrahydropyrimidin-2(1H)-one (96.2 mg).

(5) 3'-(N-(3-(3-(4-ethoxyphenyl)-2-oxotetrahydropyrimidin-1(2H)-yl)phenyl)sulfamoyl)-4'-methoxy-N,N-dimethyl-[1,1'-biphenyl]-3-carboxamide

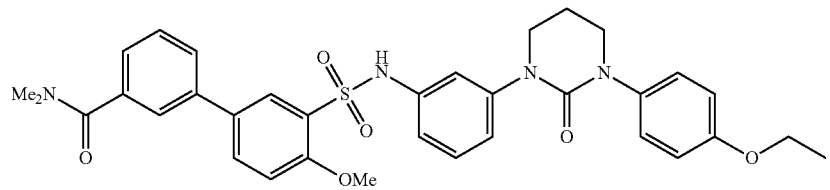 [SMILES: CCOc1ccc(N2CCCN(c3cccc(NS(=O)(=O)c4cc(-c5cccc(C(=O)N(C)C)c5)ccc4OC)c3)C2=O)cc1]

Under an argon atmosphere, to a solution of 1-(3-aminophenyl)-3-(4-ethoxyphenyl)tetrahydropyrimidin-2(1H)-one (50.4 mg) in anhydrous pyridine (2.0 mL) was added 3'-(dimethylcarbamoyl)-4-methoxy-[1,1'-biphenyl]-3-sulfonyl chloride (56.9 mg), and the mixture was stirred at room temperature for 1 hr. The reaction mixture was concentrated under reduced pressure, and the obtained residue was purified by silica gel column chromatography (eluent: ethyl acetate) to give 3'-(N-(3-(3-(4-ethoxyphenyl)-2-oxotetrahydropyrimidin-1(2H)-yl)phenyl)sulfamoyl)-4'-methoxy-N,N-dimethyl-[1,1'-biphenyl]-3-carboxamide (91.9 mg).

The compounds (Examples 7-11) described in the following Table 2 were also synthesized similarly from alkyl halide having the corresponding R group.

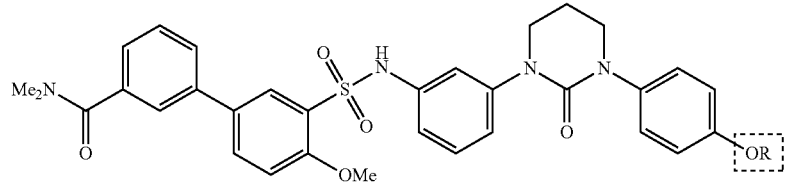

TABLE 2

| Ex. No. | OR | $^1$H-NMR |
|---|---|---|
| 6 | OEt | 1H NMR (400 MHz, CDCl3) δ 1.39 (t, J = 7.2 Hz, 3H), 2.18 (p, J = 6.0 Hz, 2H), 2.99 (s, 3H), 3.13 (s, 3H), 3.68-3.72 (m, 4H), 3.98 (s, 3H), 3.99 (q, J = 7.2 Hz, 2H), 6.80-6.85 (m, 3H), 7.04 (d, J = 8.4 Hz, 1H), 7.07-7.13 (m, 3H), 7.19 (d, J = 8.8 Hz, 2H),7.30 (s, 1H), 7.34 (ddd, J = 8.0, 1.6, 1.2 Hz, 1H), 7.39-7.43 (m, 1H), 7.52-7.55 (m, 2H), 7.68 (dd, J = 8.4, 2.0 Hz, 1H), 8.06 (d, J = 2.0 Hz, 1H). |
| 7 | OnPr | 1H NMR (400 MHz, CDCl3): δ 0.96 (t, J = 7.3 Hz, 3H), 1.47 (qt, J = 7.3, 7.3 Hz, 2H), 1.74 (tt, J = 7.3, 6.4 Hz, 2H), 2.18 (tt, J = 5.5, 5.5 Hz, 2H), 2.99 (s, 3H), 3.13 (s, 3H), 3.70 (t, J = 5.5 Hz, 2H), 3.71 (t, J = 5.5 Hz, 2H), 3.92 (t, J = 6.4 Hz, 2H), 3.96-4.02 (m, 3H), 6.79-6.83 (m, 1H), 6.83 (d, J = 9.2 Hz, 2H), 7.01-7.15 (m, 4H), 7.18 (d, J = 9.2 Hz, 2H), 7.25-7.32 (m, 1H), 7.34 (dt, J = 7.8, 1.4 Hz, 1H), 7.41 (dd, J = 7.8, 7.8 Hz, 1H), 7.51-7.56 (m, 2H), 7.68 (dt, J = 8.7, 2.3 Hz, 1H), 8.05 (d, J= 2.3 Hz, 1H). |
| 8 | OnBu | 1H NMR (400 MHz, CDCl3): δ 0.91 (t, J = 7.3 Hz, 3H), 1.28-1.40 (m, 2H), 1.57 (p, J = 7.68 Hz, 2H), 2.18 (p, J = 5.8 Hz, 2H), 2.57 (t, J = 7.7 Hz, 2H), 2.98 (s, 3H), 3.12 (s, 3H), 3.69 (t, J = 5.7 Hz, 2H), 3.74 (t, J = 6.0 Hz, 2H), 3.98 (s, 3H), 6.77-6.87 (m, 1H), 7.00-7.15 (m, 6H), 7.15-7.24 (m, 2H), 7.28-7.37 (m, 2H), 7.37-7.45 (m, 1H), 7.47-7.60 (m, 2H) 7.68 (dd, J = 2.3, 8.7 Hz, 1H), 8.06 (d, J = 2.3 Hz, 1H). |
| 9 | OCH$_2$CF$_3$ | 1H NMR (400 MHz, CDCl3): δ 2.21 (p, J = 6.0 Hz, 2H), 2.99 (s, 3H), 3.13 (s, 3H), 3.73 (t, J = 6.0 Hz, 2H), 3.73 (t, J = 6.0 Hz, 2H), 4.02 (s, 3H), 4.32 (p, J = 8.2 Hz, 2H), 6.82 (dt, J = 6.4, 2.3 Hz, 1H), 6.90 (d, J = 9.2 Hz, 2H), 7.05 (s, 1H), 7.07 (d, J = 8.7 Hz, 1H), 7.09-7.17 (m, 3H), 7.24 (d, J = 9.2 Hz, 2H), 7.35 (dt, J = 7.3, 1.4 Hz, 1H), 7.38-7.45 (m, 1H), 7.52-7.57 (m, 2H), 7.71 (dd, J = 8.7, 2.3 Hz, 1H), 8.06 (d, J = 2.3 Hz, 1H). |
| 10 | OiBu | 1H NMR (400 MHz, CDCl3): δ 1.00 (d, J = 6.9 Hz, 6H), 2.00-2.12 (m, 1H), 2.19 (p, J = 6.4 Hz, 2H), 2.99 (s, 3H), 3.13 (s, 3H), 3.67-3.75 (m, 6H), 4.03 (s, 3H) 6.79-6.88 (m, 3H), 7.04-7.15 (m, 5H), 7.18 (dd, J = 6.9, 1.8 Hz, 2H), 7.35 (dt, J = 8.0, 1.4 Hz, 1H), 7.38-7.45 (m, 1H), 7.51-7.67 (m, 1H) 7.70 (dd, J = 8.5, 2.5 Hz, 1H), 8.06 (d, J = 2.3 Hz, 1H). |
| 11 | OnOct | 1H NMR (400 MHz, CDCl3): δ 0.88 (t, J = 6.9 Hz, 3H), 1.24-1.38 (m, 8H), 1.43 (p, J = 6.6 Hz, 2H), 1.75 (p, J = 6.6 Hz, 2H), 2.17 (p, J = 5.72 Hz, 2H), 2.98 (s, 3H), 3.12 (s, 3H), 3.65-3.73 (m, 4H), 3.88-3.93 (t, J = 6.6 Hz, 2H), 3.94 (s, 3H), 6.78-6.86 (m, 3H), 7.00-7.10 (m, 3H), 7.12 (s, 1H), 7.15-7.22 (m, 2H), 7.30-7.37 (m, 1H), 7.37-7.44 (m, 1H), 7.44-7.59 (m, 3H), 7.67 (dd, J = 2.5, 8.2 Hz, 1H), 8.06 (d, J = 2.3 Hz, 1H). |

Production Example (3)

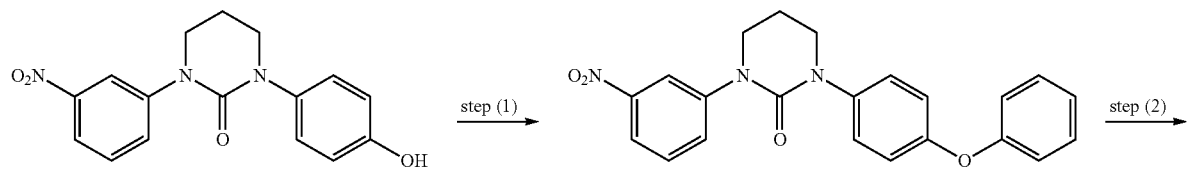

(1) 1-(3-nitrophenyl)-3-(4-phenoxyphenyl)tetrahydropyrimidin-2(1H)-one

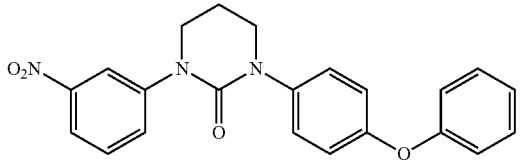 [SMILES: O=C1N(c2ccc(Oc3ccccc3)cc2)CCCN1c1cccc([N+](=O)[O-])c1]

Under an argon atmosphere, to a solution of 1-(4-hydroxyphenyl)-3-(3-nitrophenyl)tetrahydropyrimidin-2(1H)-one (50.0 mg) in anhydrous pyridine (600 μL) were added copper powder (5.60 mg), anhydrous potassium carbonate (50.7 mg) and bromobenzene (108 mg), and the mixture was stirred under heating under reflux for 10 hr. The reaction mixture was allowed to cool, filtered through Celite, and washed with chloroform. The filtrate was concentrated under reduced pressure, and the obtained residue was purified by preparative thin layer chromatography (eluent: chloroform/methanol=3.3%) to give 1-(3-nitrophenyl)-3-(4-phenoxyphenyl)tetrahydropyrimidin-2(1H)-one (14.9 mg).

(2) 4'-methoxy-N, N-dimethyl-3'-(N-(3-(2-oxo-3-(4-phenoxyphenyl)tetrahydropyrimidin-1(2H)-yl)phenyl)sulfamoyl)-[1,1'-biphenyl]-3-carboxamide

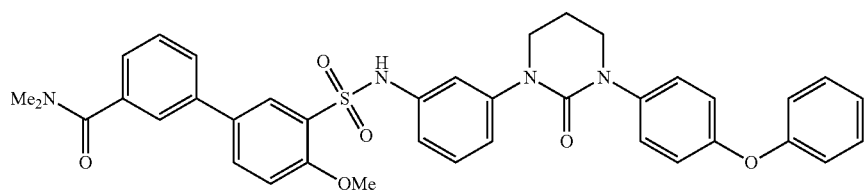 [SMILES: COc1ccc(-c2cccc(C(=O)N(C)C)c2)cc1S(=O)(=O)Nc1cccc(N2CCCN(c3ccc(Oc4ccccc4)cc3)C2=O)c1]

To a solution of 1-(3-nitrophenyl)-3-(4-phenoxyphenyl)tetrahydropyrimidin-2(1H)-one (14.0 mg) in ethanol (500 μL) was added 5% palladium-activated carbon (14.0 mg), and the mixture was stirred under a hydrogen atmosphere at room temperature for 1 hr. The reaction mixture was allowed to cool and filtered through Celite, and the filtrate was concentrated. The obtained residue was dissolved in pyridine (150 μL), a solution of 3'-(dimethylcarbamoyl)-4-methoxy-[1,1'-biphenyl]-3-sulfonyl chloride (25.4 mg) in dichloromethane (300 μL) was added, and the mixture was stirred at room temperature for 6 hr. The reaction mixture was concentrated under reduced pressure, and the obtained residue was purified by preparative thin layer chromatography (eluent: ethyl acetate) to give 4'-methoxy-N,N-dimethyl-3'-(N-(3-(2-oxo-3-(4-phenoxyphenyl)tetrahydropyrimidin-1(2H)-yl)phenyl)sulfamoyl)-[1,1'-biphenyl]-3-carboxamide (5.3 mg).

Production Example (4)

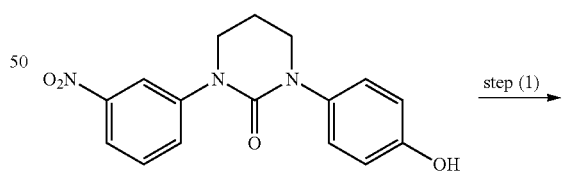

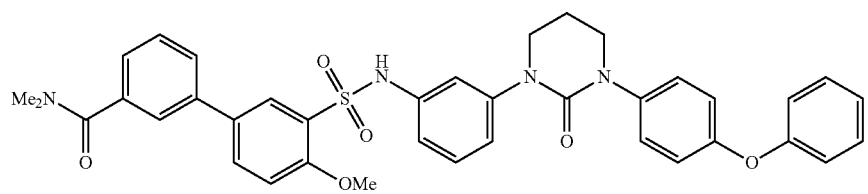

-continued

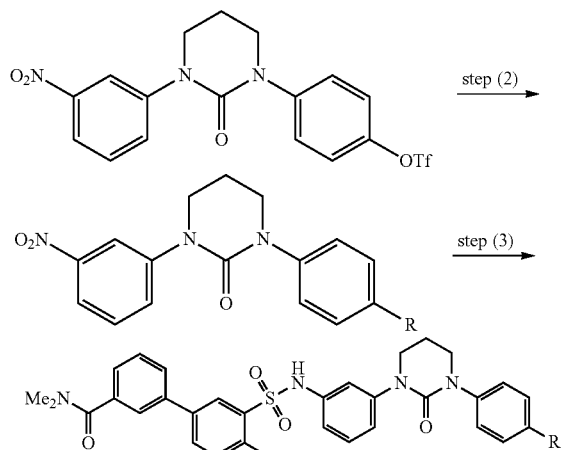

Under an argon atmosphere, to a solution of 4-(3-(3-nitrophenyl)-2-oxotetrahydropyrimidin-1(2H)-yl)phenyl trifluoromethanesulfonate (56.9 mg) in 1,4-dioxane (1.3 mL) were added butylboronic acid (26.0 mg), potassium phosphate (81.4 mg) and tetrakis(triphenylphosphine)palladium (7.4 mg), and the mixture was heated under reflux for 8 hr. The reaction mixture was filtered through Celite, washed with ethyl acetate, and the filtrate was concentrated. The obtained residue was purified by silica gel column chromatography (eluent: ethyl acetate/hexane=33%) to give 1-(4-butylphenyl)-3-(3-nitrophenyl)tetrahydropyrimidin-2(1H)-one (22.1 mg).

(3) 3'-(N-(3-(3-(4-butylphenyl)-2-oxotetrahydropyrimidin-1(2H)-yl)phenyl)sulfamoyl)-4'-methoxy-N,N-dimethyl-[1,1'-biphenyl]-3-carboxamide

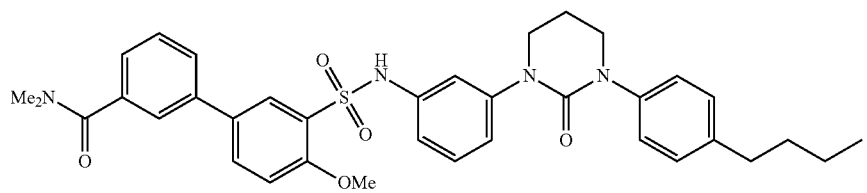

(1) 4-(3-(3-nitrophenyl)-2-oxotetrahydropyrimidin-1(2H)-yl)phenyl Trifluoromethanesulfonate To a solution of 1-(4-butylphenyl)-3-(3-nitrophenyl)tetrahydropyrimidin-2(1H)-one (22.0 mg) in ethanol (780 µL) was added 5% palladium-activated carbon (22.0 mg), and the mixture was stirred under a hydrogen atmosphere at room temperature for 1 hr. The reaction mixture was allowed to cool and filtered through Celite, and the filtrate was concentrated. The obtained residue was dissolved in pyridine (1.3 mL), a solution of 3'-(dimethylcarbamoyl)-4-methoxy-[1,1'-biphenyl]-3-sulfonyl chloride (22.0 mg) in dichloromethane (300 µL) was added, and the mixture was stirred at room temperature for 3 hr. The reaction mixture was concentrated under reduced pressure, and the obtained residue was purified by silica gel column chromatography (eluent: ethyl acetate) to give 3'-(N-(3-(3-(4-butylphenyl)-2-oxotetrahydropyrimidin-1(2H)-yl)phenyl)sulfamoyl)-4'-methoxy-N,N-dimethyl-[1,1'-biphenyl]-3-carboxamide (28.8 mg).

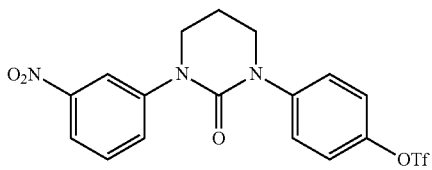 [SMILES: O=C1N(c2ccc(OS(=O)(=O)C(F)(F)F)cc2)CCCN1c1cccc([N+](=O)[O-])c1]

Under an argon atmosphere, to a solution of 1-(4-hydroxyphenyl)-3-(3-nitrophenyl)tetrahydropyrimidin-2(1H)-one (50.0 mg) in dichloromethane (1.6 mL) were added potassium carbonate (44.1 mg) and N,N-bis(trifluoromethylsulfonyl)aniline (70.3 mg), and the mixture was stirred at room temperature for 1.5 hr. To the reaction mixture was added pure water, and the mixture was extracted with chloroform. The organic layer was dried over sodium sulfate and filtered, and the filtrate was concentrated. The obtained residue was purified by silica gel column chromatography (eluent: ethyl acetate/hexane=12%-88%) to give 4-(3-(3-nitrophenyl)-2-oxotetrahydropyrimidin-1(2H)-yl)phenyl trifluoromethanesulfonate (68.8 mg).

(2) 1-(4-butylphenyl)-3-(3-nitrophenyl)tetrahydropyrimidin-2(1H)-one

The compounds (Examples 14 and 15) described in the following Table 3 were also synthesized similarly from boronic acid having the corresponding R group.

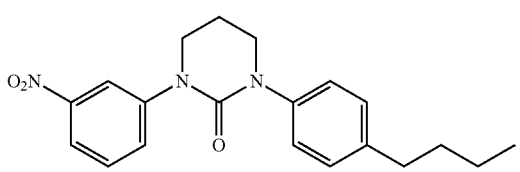 [SMILES: CCCCc1ccc(N2CCCN(c3cccc([N+](=O)[O-])c3)C2=O)cc1]

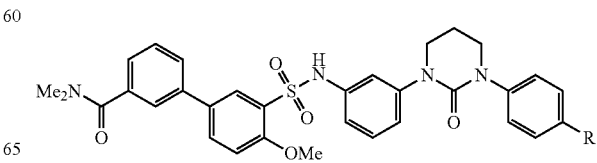

TABLE 3

| Ex. No. | R | ¹H-NMR |
|---|---|---|
| 12 | OPh | 1H NMR (400 MHz, CDCl3): δ 2.21 (p, J = 5.8 Hz, 2H), 2.99 (s, 3H), 3.13 (s, 3H), 3.66-3.82 (m, 4H), 4.02 (s, 3H), 6.77-6.88 (m, 1H), 6.93-7.03 (m, 4H), 7.04-7.17 (m, 6H), 7.23-7.25 (m, 1H), 7.28-7.37 (m, 4H), 7.38-7.45 (m, 1H), 7.50-7.58 (m, 2H), 7.70 (dd, J = 2.5, 8.5 Hz, 1H), 8.06 (d, J = 2.3 Hz, 1H). |
| 13 | nBu | 1H NMR (400 MHz, CDCl3): δ 0.91 (t, J = 7.33 Hz, 3H), 1.28-1.42 (m, 2H), 1.57 (p, J = 7.79 Hz, 2H), 2.18 (p, J = 5.95 Hz, 2H), 2.57 (t, J = 7.79 Hz, 2H), 2.98 (s, 3H), 3.12 (s, 3H), 3.69 (t, J = 5.95 Hz, 2H), 3.74 (t, J = 5.95 Hz, 2H), 3.98 (s, 3H), 6.77-6.87 (m, 1H), 7.04 (d, J = 9.16 Hz, 1H), 7.07-7.16 (m, 5H), 7.19 (d, J = 8.24 Hz, 2H), 7.31 (s, 1H), 7.34 (dt, J = 1.37, 7.33 Hz, 1H), 7.40 (t, J = 7.33 Hz, 1H), 7.49-7.58 (m, 2H), 7.68 (dd, J = 2.29, 8.70 Hz, 1H), 8.06 (d, J = 2.29 Hz, 1H). |
| 14 | Ph | 1H NMR (400 MHz, CDCl3): δ 2.22 (p, J = 5.84 Hz, 2H), 2.98 (s, 3H), 3.12 (s, 3H), 3.72 (t, J = 6.0 Hz, 2H), 3.81 (t, J = 6.0 Hz, 2H), 3.99 (s, 3H), 6.78-6.87 (m, 1H), 7.05 (d, J = 8.7 Hz, 1H), 7.10 (d, J = 5.0 Hz, 2H), 7.17 (s, 1H), 7.28 (s, 1H), 7.30-7.46 (m, 7H), 7.49-7.62 (m, 6H) 7.69 (dd, J = 2.5, 8.5 Hz, 1H), 8.07 (d, J = 2.3 Hz, 1H). |
| 15 | nOct | 1H NMR (400 MHz, CDCl3): δ 0.88 (t, J = 6.87 Hz, 3H), 1.20-1.36 (m, 10H), 1.58 (p, J = 7.10 Hz, 2H), 2.19 (p, J = 5.95 Hz, 2H), 2.56 (t, J = 7.79 Hz, 2H), 2.99 (s, 3H), 3.13 (s, 3H), 3.63-3.79 (m, 4H), 3.98 (s, 3H), 6.77-6.87 (m, 1H), 7.04 (d, J = 8.70 Hz, 1H), 7.07-7.16 (m, 5H), 7.19 (d, J = 8.70 Hz, 2H), 7.28 (m, 1H), 7.34 (dt, J = 1.37, 7.79Hz, 1H), 7.40 (t, J = 7.79 Hz, 1H), 7.49-7.59 (m, 2H), 7.68 (dd, J = 2.29, 8.70 Hz, 1H), 8.06 (d, J = 2.29 Hz, 1H). |

Production Example (5)

(1) 4'-hydroxy-N,N-dimethyl-[1,1'-biphenyl]-3-carboxamide

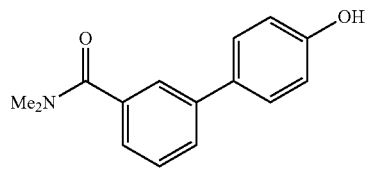 [SMILES: CN(C)C(=O)c1cccc(-c2ccc(O)cc2)c1]

Under an argon atmosphere, to a solution of 4-bromophenol (1.03 g) in DME (25.0 mL) were added 3-(N,N-dimethylaminocarbonyl)phenylboronic acid (1.04 g), sodium carbonate (1.12 g), water (2.50 mL) and tetrakis(triphenylphosphine)palladium (219.3 mg), and the mixture was heated under reflux for 16 hr. To the reaction mixture was added pure water, and the mixture was extracted with chloroform. The organic layer was dried over sodium sulfate and filtered, and the filtrate was concentrated. The obtained residue was purified by silica gel column chromatography (eluent: hexane/ethyl acetate=4/1-+1/1) to give 4'-hydroxy-N,N-dimethyl-[1,1'-biphenyl]-3-carboxamide (459.8 mg).

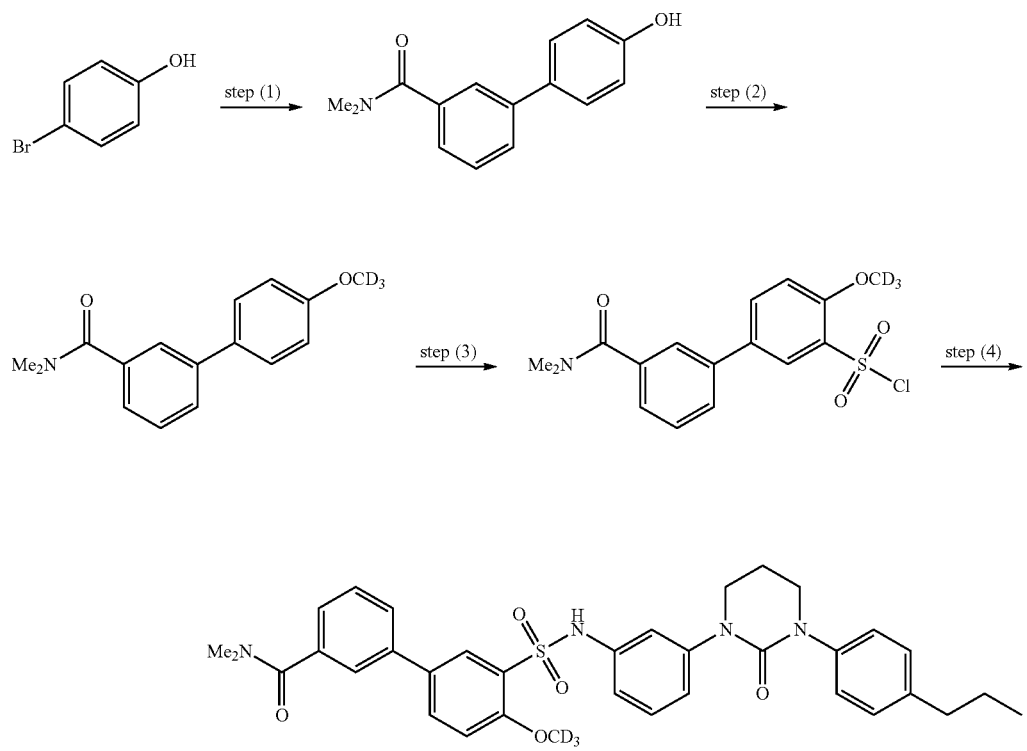

(2) 4'-(methoxy-d3)-N,N-dimethyl-[1,1'-biphenyl]-3-carboxamide

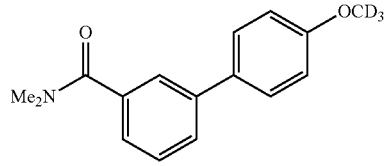

Under an argon atmosphere, to a solution of 4'-hydroxy-N,N-dimethyl-[1,1'-biphenyl]-3-carboxamide (165 mg) in DMF (7.0 mL) were added potassium carbonate (189 mg) and iodomethane-d3 (166 μL), and the mixture was stirred at room temperature for 4 hr. To the reaction mixture was added pure water, and the mixture was extracted with chloroform. The organic layer was dried over sodium sulfate and filtered, and the filtrate was concentrated. The obtained residue was purified by silica gel column chromatography (eluent: methanol/chloroform=1.3%) to give 4'-(methoxy-d3)-N,N-dimethyl-[1,1'-biphenyl]-3-carboxamide (170 mg).

(3) 3'-(dimethylcarbamoyl)-4-(methoxy-d3)-[1,1'-biphenyl]-3-sulfonyl Chloride

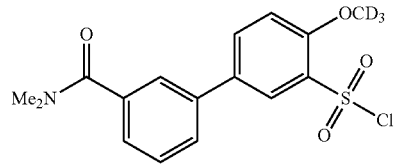

Under an argon atmosphere, to chlorosulfonic acid (500 μL) was gradually added a solution of 4'-(methoxy-d3)-N,N-dimethyl-[1,1'-biphenyl]-3-carboxamide (165 mg) in dichloromethane (3.0 mL) under ice-cooling, and the mixture was stirred for 20 min. The reaction mixture was warmed to room temperature, thionyl chloride (1.0 mL) and DMF (1 drop) were added, and the mixture was stirred at 60° C. for 1.5 hr. The reaction mixture was allowed to cool, poured into ice, stirred for 20 min, and extracted with chloroform. The organic layer was dried over sodium sulfate and filtered, and the filtrate was concentrated under reduced pressure. The obtained residue was purified by silica gel column chromatography (eluent: ethyl acetate/chloroform=2.5%-5%) to give 3'-(dimethylcarbamoyl)-4-(methoxy-d3)-[1,1'-biphenyl]-3-sulfonyl chloride (153 mg).

(4) 4'-(methoxy-d3)-N,N-dimethyl-3'-(N-(3-(2-oxo-3-(4-propylphenyl)tetrahydropyrimidin-1(2H)-yl)phenyl)sulfamoyl)-[1,1'-biphenyl]-3-carboxamide

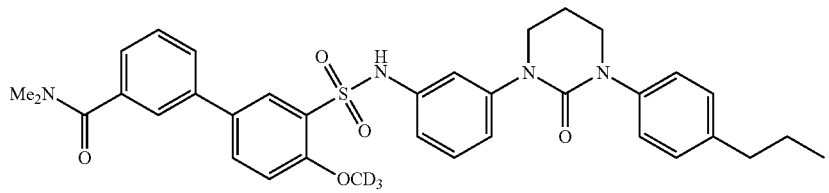

Under an argon atmosphere, to a solution of 1-(3-aminophenyl)-3-(4-propylphenyl)tetrahydropyrimidin-2(1H)-one (17.5 mg) in anhydrous pyridine (1.50 mL) was added a solution of 3'-(dimethylcarbamoyl)-4-(methoxy-d3)-[1,1'-biphenyl]-3-sulfonyl chloride (21.2 mg) in dichloromethane (800 μL), and the mixture was stirred at room temperature for 1 hr. To the reaction mixture was added distilled water, and the mixture was extracted with chloroform. The organic layer was washed with saturated brine, dried over magnesium sulfate and filtered, and the filtrate was concentrated under reduced pressure. The obtained residue was purified by silica gel column chromatography (eluent: ethyl acetate). The obtained solid was dissolved in chloroform, and the solution was added to ice-cooled hexane by small portions, and the resulting precipitate was filtered to give 4'-(methoxy-d3)-N,N-dimethyl-3'-(N-(3-(2-oxo-3-(4-propylphenyl)tetrahydropyrimidin-1(2H)-yl)phenyl)sulfamoyl)-[1,1'-biphenyl]-3-carboxamide (27.5 mg).

Production Example (6)

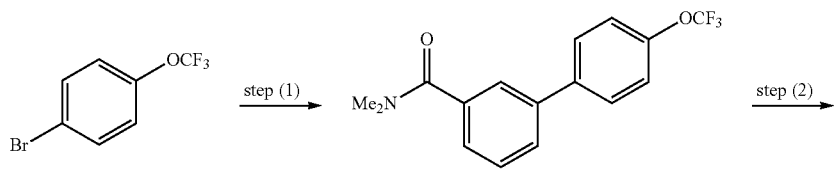

-continued

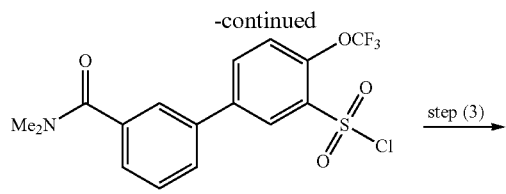

step (3)

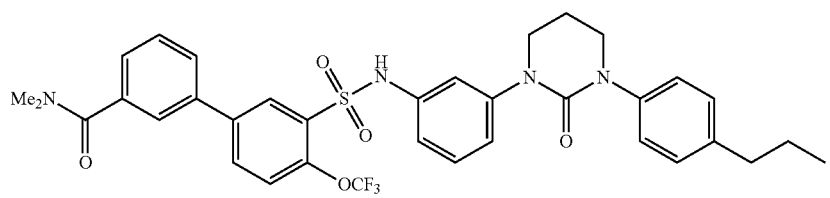

(1) N,N-dimethyl-4'-(trifluoromethoxy)-[1,1'-biphenyl]-3-carboxamide (2) 3'-(dimethylcarbamoyl)-4-(trifluoromethoxy)-[1,1'-biphenyl]-3-sulfonyl Chloride

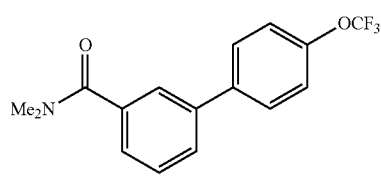 [SMILES: CN(C)C(=O)c1cccc(-c2ccc(OC(F)(F)F)cc2)c1]

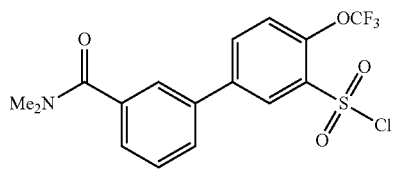 [SMILES: CN(C)C(=O)c1cccc(-c2ccc(OC(F)(F)F)c(S(=O)(=O)Cl)c2)c1]

Under an argon atmosphere, to a solution of 1-bromo-4-trifluoromethoxybenzene (350 μL) in DME (24.0 mL) were added 3-(N,N-dimethylaminocarbonyl)phenylboronic acid (501 mg), sodium carbonate (500 g), water (2.0 mL) and tetrakis(triphenylphosphine)palladium (58.0 mg), and the mixture was heated under reflux overnight. The reaction mixture was filtered through Celite, and the filtrate was concentrated. To the obtained residue was added pure water, and the mixture was extracted with chloroform. The organic layer was dried over sodium sulfate and filtered, and the filtrate was concentrated under reduced pressure. The obtained residue was purified by silica gel column chromatography (eluent: ethyl acetate/hexane=25%→100%) to give N,N-dimethyl-4'-(trifluoromethoxy)-[1,1'-biphenyl]-3-carboxamide (590 mg).

Under an argon atmosphere, to chlorosulfonic acid (1.50 mL) was gradually added a solution of N,N-dimethyl-4'-(trifluoromethoxy)-[1,1'-biphenyl]-3-carboxamide (587 mg) in dichloromethane (3.0 mL) under ice-cooling, and the mixture was stirred at room temperature overnight. The reaction mixture was warmed to 60° C. and further stirred for 6 hr. The reaction mixture was allowed to cool, poured into ice, stirred for 20 min, and extracted with chloroform. The organic layer was dried over sodium sulfate and filtered, and the filtrate was concentrated under reduced pressure. The obtained residue was purified by silica gel column chromatography (eluent: ethyl acetate/hexane=25%-100%) to give 3'-(dimethylcarbamoyl)-4-(trifluoromethoxy)-[1,1'-biphenyl]-3-sulfonyl chloride as a 7:1 mixture (620 mg) with the regioisomer.

(3) N,N-dimethyl-3'-(N-(3-(2-oxo-3-(4-propylphenyl)tetrahydropyrimidin-1(2H)-yl)phenyl)sulfamoyl)-4'-(trifluoromethoxy)-[1,1'-biphenyl]-3-carboxamide

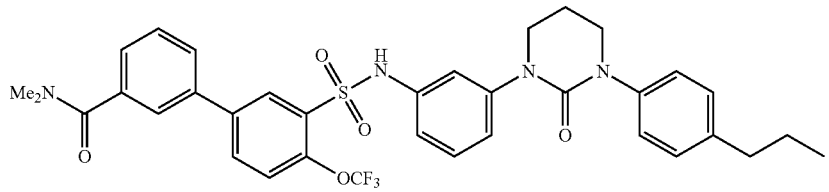 [SMILES: CCCc1ccc(N2CCCN(c3cccc(NS(=O)(=O)c4cc(-c5cccc(C(=O)N(C)C)c5)ccc4OC(F)(F)F)c3)C2=O)cc1]

Under an argon atmosphere, to a solution of 1-(3-aminophenyl)-3-(4-propylphenyl)tetrahydropyrimidin-2(1H)-one (32.4 mg) in anhydrous pyridine (1.50 mL) was added a solution of a regioisomer mixture (43.5 mg) of 3'-(dimethylcarbamoyl)-4-(trifluoromethoxy)-[1,1'-biphenyl]-3-sulfonyl chloride in dichloromethane (1.6 mL), and the mixture was stirred at room temperature for 2 hr. The reaction mixture was concentrated under reduced pressure, and the obtained residue was purified by preparative thin layer chromatography (eluent: methanol/chloroform=6.6%). The obtained solid was dissolved in chloroform, and the solution was added to ice-cooled hexane by small portions, and the resulting precipitate was filtered to give N,N-dimethyl-3'-(N-(3-(2-oxo-3-(4-propylphenyl)tetrahydropyrimidin-1(2H)-yl)phenyl)sulfamoyl)-4'-(trifluoromethoxy)-[1,1'-biphenyl]-3-carboxamide (51.1 mg).

Production Example (7)

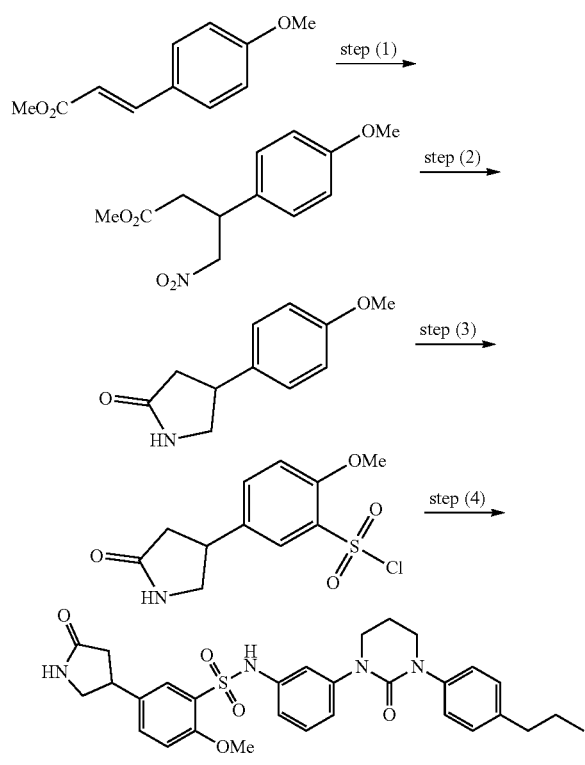

(1) methyl 3-(4-methoxyphenyl)-4-nitrobutanoate

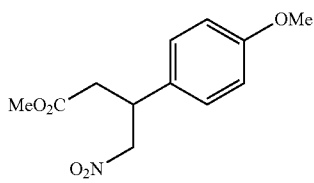

(i) Under an argon atmosphere, to a solution of 4-methoxycinnamic acid (502 mg) in methanol (10.0 mL) was added under ice-cooling sulfuric acid (500 μL), and the mixture was heated under reflux for 7 hr. The reaction mixture was allowed to cool, pure water was added, and the mixture was extracted with chloroform. The organic layer was washed with saturated brine, dried over sodium sulfate and filtered, and the filtrate was concentrated under reduced pressure. The obtained residue was purified by silica gel column chromatography (eluent: chloroform) to give methyl 4-methoxycinnamate (497 mg).

(ii) Under an argon atmosphere, to a solution of methyl 4-methoxycinnamate (494 mg) in nitromethane (9.0 mL) was added under ice-cooling DBU (422 μL), and the mixture was stirred at room temperature overnight. To the reaction mixture was added saturated aqueous sodium hydrogen carbonate solution, and the mixture was extracted with ethyl acetate. The organic layer was washed with saturated brine, dried over sodium sulfate and filtered, and the filtrate was concentrated under reduced pressure. The obtained residue was purified by silica gel column chromatography (eluent: ethyl acetate/hexane=20%) to give methyl 3-(4-methoxyphenyl)-4-nitrobutanoate (647 mg).

(2) 4-(4-methoxyphenyl)pyrrolidin-2-one

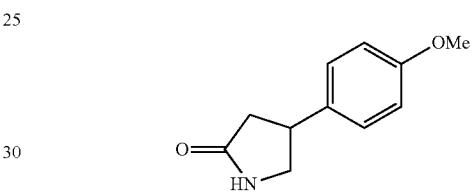

Under an argon atmosphere, to a solution of methyl 3-(4-methoxyphenyl)-4-nitrobutanoate (640 mg) in 2-propanol (45 mL) were added 1 M HCl aqueous solution (25 mL) and zinc powder (6.6 g), and the mixture was stirred at 60° C. for 1 hr. The reaction mixture was filtered through Celite and washed with chloroform, and the filtrate was concentrated. The obtained residue was adjusted to pH9 with aqueous ammonia, and extracted with chloroform. The organic layer was washed with saturated brine, dried over sodium sulfate and filtered, and the filtrate was concentrated under reduced pressure. The obtained residue was purified by silica gel column chromatography (eluent: ethyl acetate/hexane/10% ammonia methanol=1/1/0.1) to give 4-(4-methoxyphenyl)pyrrolidin-2-one (395 mg).

(3) 2-methoxy-5-(5-oxopyrrolidin-3-yl)benzenesulfonyl Chloride

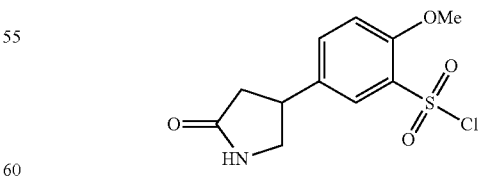

Under an argon atmosphere, to chlorosulfonic acid (1.0 mL) was gradually added a solution of 4-(4-methoxyphenyl)pyrrolidin-2-one (50.2 mg) in dichloromethane (2.0 mL) under ice-cooling, and the mixture was stirred at room temperature for 30 min. The reaction mixture was poured into ice, stirred for 20 min, and extracted with dichloromethane. The organic layer was washed with saturated brine, dried over sodium sulfate and filtered, and the filtrate was concentrated under reduced pressure to give 2-methoxy-5-(5-oxopyrrolidin-3-yl)benzenesulfonyl chloride (61.5 mg).

(4) 2-methoxy-N-(3-(2-oxo-3-(4-propylphenyl)tetrahydropyrimidin-1(2H)-yl)phenyl)-5-(5-oxopyrrolidin-3-yl)benzenesulfonamide

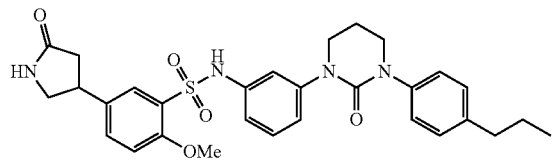 [SMILES: CCCc1ccc(N2CCCN(c3cccc(NS(=O)(=O)c4cc(C5CNC(=O)C5)ccc4OC)c3)C2=O)cc1]

Under an argon atmosphere, to a solution of 1-(3-aminophenyl)-3-(4-propylphenyl)tetrahydropyrimidin-2(1H)-one (17.6 mg) in anhydrous pyridine (460 μL) was added a solution of 2-methoxy-5-(5-oxopyrrolidin-3-yl)benzenesulfonyl chloride (20.0 mg) in dichloromethane (1.6 mL), and the mixture was stirred at room temperature for 1 hr. To the reaction mixture was added saturated aqueous sodium hydrogen carbonate solution, and the mixture was extracted with chloroform. The organic layer was washed with saturated brine, dried over sodium sulfate and filtered, and the filtrate was concentrated under reduced pressure. The obtained residue was purified by preparative thin layer chromatography (eluent: methanol/chloroform=16.6%). The obtained solid was dissolved in chloroform, and the solution was added to ice-cooled-hexane by small portions, and the resulting precipitate was filtered to give 2-methoxy-N-(3-(2-oxo-3-(4-propylphenyl)tetrahydropyrimidin-1(2H)-yl)phenyl)-5-(5-oxopyrrolidin-3-yl)benzenesulfonamide (31.5 mg).

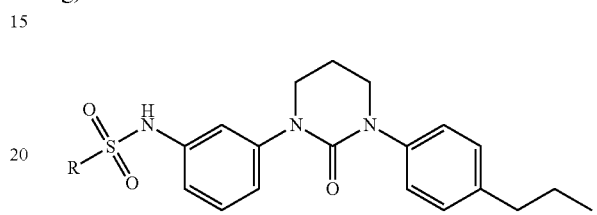

TABLE 4

| Ex. No. | R | $^1$H-NMR |
|---|---|---|
| 16 | Me$_2$N-C(O)-[phenyl]-[phenyl]-OCD$_3$ (with attachment point) | 1H-NMR (400 MHz, CDCl3) δ 0.93 (t, J = 7.3 Hz, 3H), 1.59-1.66 (m, 2H), 2.20 (p, J = 5.5 Hz, 2H), 2.55 (t, J = 7.6 Hz, 2H), 2.99 (s, 3H), 3.13 (s, 3H), 3.71-3.77 (m, 4H), 6.82-6.85 (m, 1H), 6.97 (s, 1H), 7.07 (d, J = 8.7 Hz, 1H), 7.11-7.14 (m, 5H), 7.18-7.20 (m, 2H), 7.35 (d, J = 7.8 Hz, 1H), 7.41 (dd, J = 8.2, 7.8 Hz, 1H), 7.54-7.55 (m, 2H), 7.70 (dd, J = 8.7, 2.3 Hz, 1H), 8.06 (d, J = 2.3 Hz, 1H). |
| 17 | Me$_2$N-C(O)-[phenyl]-[phenyl]-OCF$_3$ (with attachment point) | 1H-NMR (400 MHz, Pyridine-d5) δ 0.86 (t, J = 7.3 Hz, 3H), 1.53-1.59 (m, 2H), 1.92 (p, J = 6.0, 2H), 2.50 (t, J = 7.6 Hz, 2H), 2.82 (s, 3H), 3.07 (s, 3H), 3.58-3.62 (m, 4H), 7.19-7.22 (m, 3H), 7.28 (dd, J = 8.7, 8.6 Hz, 1H), 7.39-7.43 (m, 4H), 7.52-7.54 (m, 1H), 7.58 (dd, J = 8.7, 1.4 Hz, 1H), 7.71 (dt, J = 7.8, 1.3 Hz, 1H), 7.79 (dd, J = 8.7, 2.5 Hz, 1H), 7.81 (dd, J = 1.4, 1.3 Hz, 1H), 8.02 (t, J = 2.1 Hz, 1H), 8.67 (d, J = 2.5 Hz, 1H). The NH peak/signal was not observed. |
| 18 | 5-oxopyrrolidin-3-yl-[phenyl]-OMe (with attachment point) | 1H NMR (400 MHz, CDCl3) δ 0.93 (t, J = 7.3 Hz, 3H), 1.62 (q, J = 7.8 Hz, 2H), 2.23 (p, J = 5.8 Hz, 2H), 2.34 (ddd, J = 16.9, 6.9, 2.1 Hz, 1H), 2.56 (t, J = 7.8 Hz, 2H), 2.63 (ddd, 16.9, 6.9, 2.4 Hz, 1H), 3.15-3.25 (m, 1H), 3.48-3.60 (m, 2H), 3.70-3.81 (m, 4H), 3.95 (s, 3H), 5.79 (brs, 1H), 6.77 (ddd, J = 7.8, 2.1, 1.1 Hz, 1H), 6.92 (d, J = 8.7 Hz, 1H), 7.05 (ddd, J = 7.8, 2.3, 0.9 Hz, 1H), 7.10 (t, J = 7.8 Hz, 1H), 7.13-7.17 (m, 2H), 7.18-7.22 (m, 3H), 7.32 (dd, J = 8.7, 2.3 Hz, 1H), 7.40 (brs, 1H), 7.70 (d, J = 2.3 Hz, 1H). |

Production Example (8)

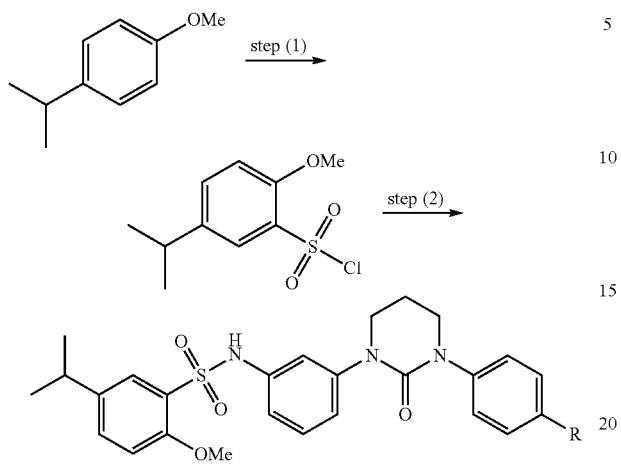

(1) 5-isopropyl-2-methoxybenzenesulfonyl Chloride

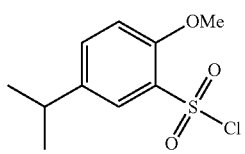

Under an argon atmosphere, to a solution of chlorosulfonic acid (2.90 mL) in dichloromethane (20 mL) was gradually added a solution of 4-isopropylanisole (2.1 mL) in dichloromethane (30 mL) under ice-cooling, and the mixture was stirred at room temperature overnight. The reaction mixture was poured into ice, and the mixture was stirred for 30 min. The resulting solid was filtered and dried under reduced pressure to give 5-isopropyl-2-methoxybenzenesulfonyl chloride (2.98 g).

(2) 5-isopropyl-2-methoxy-N-(3-(2-oxo-3-(4-propylphenyl)tetrahydropyrimidin-1(2H)-yl)phenyl)benzenesulfonamide

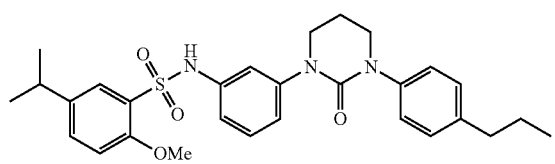 [SMILES: CCCc1ccc(N2CCCN(c3cccc(NS(=O)(=O)c4cc(C(C)C)ccc4OC)c3)C2=O)cc1]

Under an argon atmosphere, to a solution of 1-(3-aminophenyl)-3-(4-propylphenyl)tetrahydropyrimidin-2(1H)-one (32.1 mg) in anhydrous pyridine (2.10 mL) was added a solution of 5-isopropyl-2-methoxybenzenesulfonyl chloride (43.5 mg) in dichloromethane (1.6 mL), and the mixture was stirred at room temperature for 2 hr. The reaction mixture was concentrated under reduced pressure, and the obtained residue was purified by preparative thin layer chromatography (eluent: methanol/chloroform=6.6%). The obtained solid was dissolved in chloroform, and the solution was added to ice-cooled hexane by small portions, and the resulting precipitate was filtered to give 5-isopropyl-2-methoxy-N-(3-(2-oxo-3-(4-propylphenyl)tetrahydropyrimidin-1(2H)-yl)phenyl)benzenesulfonamide (51.1 mg).

The compounds (Examples 20 to 22) described in the following Table 5 were also synthesized similarly from aniline having the corresponding R group synthesized in Production Examples (1) and (2).

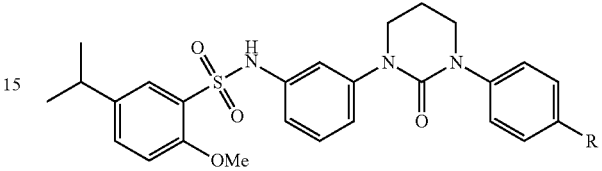

TABLE 5

| Ex. No. | R | ¹H-NMR |
|---|---|---|
| 19 | nPr | 1H NMR (400 MHz, CDCl3) δ 0.93 (t, J = 7.3 Hz, 3H), 1.17 (d, J = 6.9 Hz, 6H), 1.61 (q, J = 7.3 Hz, 2H), 2.21 (p, J = 5.9 Hz, 2H), 2.55 (dd, J = 8.4, 6.9 Hz, 2H), 2.84 (hept, J = 6.9 Hz, 1H), 3.68-3.79 (m, 4H), 3.94 (s, 3H), 6.80 (dt, J = 6.9, 2.1 Hz, 1H), 6.90 (d, J = 8.6 Hz, 1H), 7.04 (s, 1H), 7.06-7.15 (m, 5H), 7.17-7.22 (m, 2H), 7.32 (ddd, J = 8.5, 2.4, 0.5 Hz, 1H), 7.69 (d, J = 2.4 Hz, 1H). |
| 20 | iPr | 1H NMR (400 MHz, CDCl3) δ 1.17 (d, J = 6.9 Hz, 6H), 1.22 (d, J = 6.9 Hz, 6H), 2.22 (p, J = 5.9 Hz, 2H), 2.75-2.97 (m, 2H), 3.64-3.81 (m, 4H), 3.95 (s, 3H), 6.81 (dt, J = 6.7, 2.0 Hz, 1H), 6.91 (d, J = 8.5 Hz, 1H), 6.98 (s, 1H), 7.06-7.15 (m, 3H), 7.16-7.23 (m, 4H), 7.32 (dd, J = 8.5, 2.3 Hz, 1H), 7.68 (d, J = 2.3 Hz, 1H). |
| 21 | OMe | 1H NMR (400 MHz, CDCl3) δ 1.17 (d, J = 6.8 Hz, 6H), 2.21 (p, J = 6.0 Hz, 2H), 2.84 (sep, J = 6.8 Hz, 1H), 3.72 (t, J = 6.0 Hz, 2H), 3.73 (t, J = 6.0 Hz, 2H), 3.79 (s, 3H), 3.95 (s, 3H), 6.80 (ddd, J = 7.2, 2.0, 2.0 Hz, 1H), 6.86 (d, J = 9.2 Hz, 2H), 6.90 (d, J = 8.6 Hz, 1H), 7.00 (s, 1H), 7.07-7.13 (m, 3H), 7.20 (d, J = 9.2 Hz, 2H), 7.32 (dd, J = 8.6, 2.0 Hz, 1H), 7.69 (d, J = 2.0 Hz, 1H). |
| 22 | OEt | 1H NMR (400 MHz, CDCl3) δ 1.17 (d, J = 6.8 Hz, 6H), 1.39 (t, J = 7.2 Hz, 3H), 2.21 (p, J = 6.0 Hz, 2H), 2.84 (sep, J = 6.8 Hz, 1H), 3.70-3.76 (m, 4H), 3.94 (s, 3H), 4.00 (q, J = 7.2 Hz, 2H), 6.80 (ddd, J = 6.8, 2.4, 2.0 Hz, 1H), 6.85 (d, J = 8.8 Hz, 2H), 6.90 (d, J = 8.6 Hz, 1H), 7.05 (s, 1H), 7.07-7.13 (m, 3H), 7.19 (d, J = 8.8 Hz, 2H), 7.32 (dd, J = 8.6, 2.2 Hz, 1H), 7.69 (d, J = 2.2 Hz, 1H). |

Experimental Example 1

Evaluation of Agonist Activity Against OX2R

NAFT-luciferase gene and human OX2R gene were constitutively expressed in CHO cell, which is a cell line derived from Chinese hamster ovary to establish a cell line (CHOOX2R). The cells were seeded in a 96-well Multiplate at 10,000 cells/well and cultured in a 5% FBS (Thermo Scientific)-added DMEM medium (Sigma-Aldrich) for 48 hr. The medium was removed, an assay buffer (20 mM HEPES (Sigma-Aldrich), Hanks' balanced salt solution (Gibco), 0.1% BSA (Sigma-Aldrich), 2.5 mM probenecid acid (Wako Pure Chemical Industries, Ltd.)) (100 μL) containing 4 μM Fura-2AM (Cayman Chemical) was added, and the cells were incubated for 60 min. The buffer containing Fura-2AM was removed, and an assay buffer (75 μL) was added. An assay buffer (25 μL) containing a test compound was added thereto to start the reaction. Changes in the intracellular calcium ion concentration due to the reaction were measured by measuring the fluorescence intensity ratio by dual wavelength excitation at 340 and 380 nm, by using FDSS7000 (Hamamatsu Photonics K.K.). The test compound was dissolved in DMSO to 10 mM, and diluted with the assay buffer to a final concentration of $10^{-11.5}$ M to $10^{-5}$ M (final concentration of DMSO 1%). The agonist activity values ($EC_{50}$ value) of the respective compounds are shown in Table 6.

TABLE 6

| Ex. No. | EC50 (nM) |
|---|---|
| 1 | 0.610 |
| 2 | 5.12 |
| 3 | 3.10 |
| 4 | 3.30 |
| 5 | 2.41 |
| 6 | 2.87 |
| 7 | 4.47 |
| 8 | 43.0 |
| 9 | 20.0 |
| 10 | 65.9 |
| 11 | >500 |
| 12 | 217 |
| 13 | 7.52 |
| 14 | 140 |
| 15 | >500 |
| 16 | 0.843 |
| 17 | 395 |
| 18 | 6.31 |
| 19 | 19.6 |
| 20 | 41.4 |
| 21 | 81.7 |
| 22 | 38.1 |

Experimental Example 2

Awakening Effect of Oral Administration (Light Period) of Test Compound to Wild-Type Mice As the test compound, the compound of Example 1 was used.

C57BL/6J lineage wild-type (WT) mice, and orexin receptor-deficient mice (DKO mice) (both males) as a negative control were used as experimental animals. The mice (9 to 35 weeks of age) underwent surgery for embedding electroencephalogram electrodes into the skull (Bregma: X=1.5; Y=0.6, Lambda: X=1.5; Y=0) and inserting electromyogram electrodes into the trapezius muscle under isoflurane anesthesia. Two weeks postoperation were the recovery period and acclimation period to the electroencephalogram/electromyogram measurement cage, after which administration and measurement were performed. To prepare a suspension for oral administration of the test compound, the compound was grinded in an agate mortar for 20 min and sufficiently stirred while adding a small amount of 0.5% methylcellulose aqueous solution (MC). The suspension (100 μL) was dispensed into an oral gavage needle. The suspensions were prepared 30 min before administration.

To the WT mice were orally administered 100 μL each of the control MC or the test compound during the light period (ZT6) in the sleep period. The test compound was administered at concentrations of 0.625 mg/kg-25 mg/kg according to the stage. DKO mice were also evaluated by a similar method, in which MC or a test compound (5 mg/kg) was orally administered, and electroencephalogram and electromyogram were measured for 3 hr after the administration. A significant difference was not found in the awakening time after the control MC administration or the test compound administration.

Figure 3:
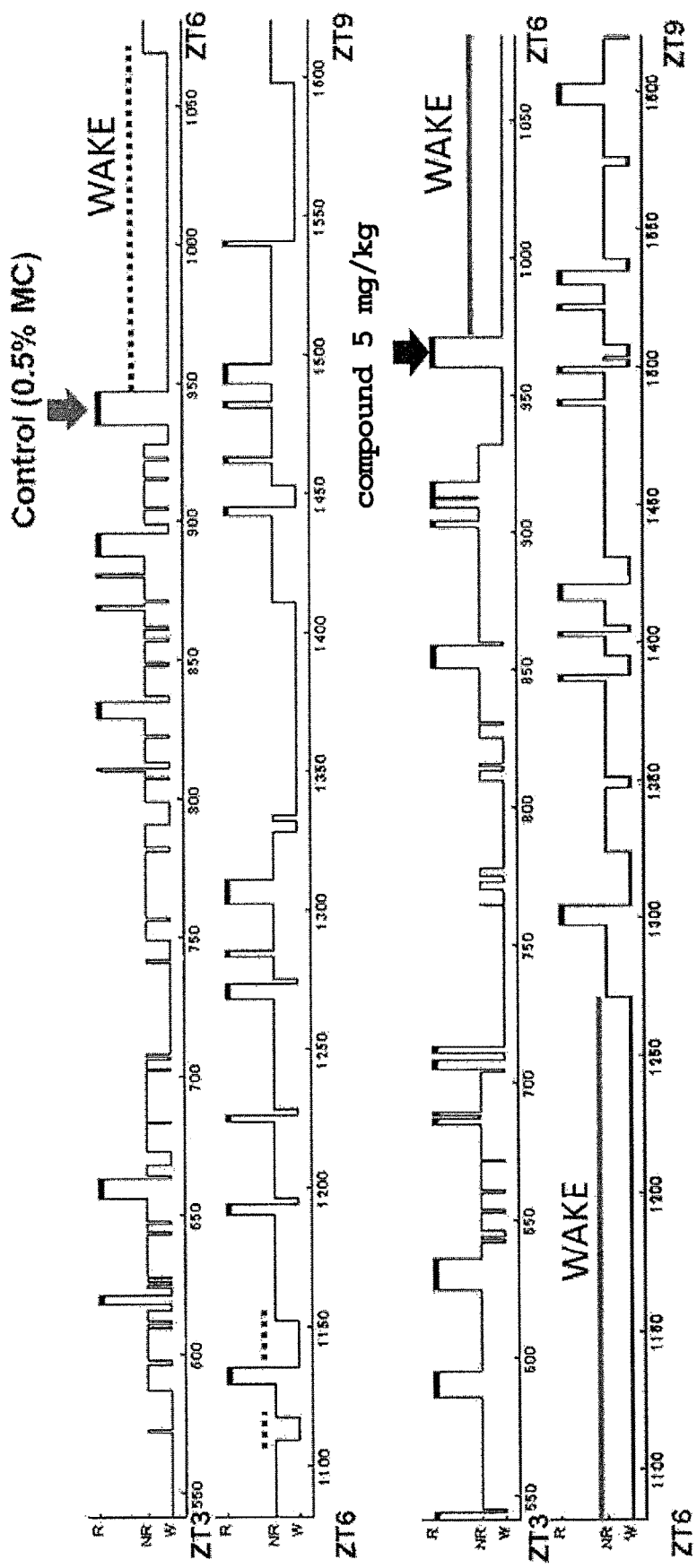
FIG. 3 shows typical hypnograms of Experimental Example 2 in which control (0.5% methylcellulose (MC) aqueous solution) or a test compound (compound of Example 1) (5 mg/kg) was orally administered to wild-type (WT) mice.

The evaluation results of the awakening prolonging effect are shown in FIG. 1, and typical hypnograms are shown in FIG. 3.

Figure 2:
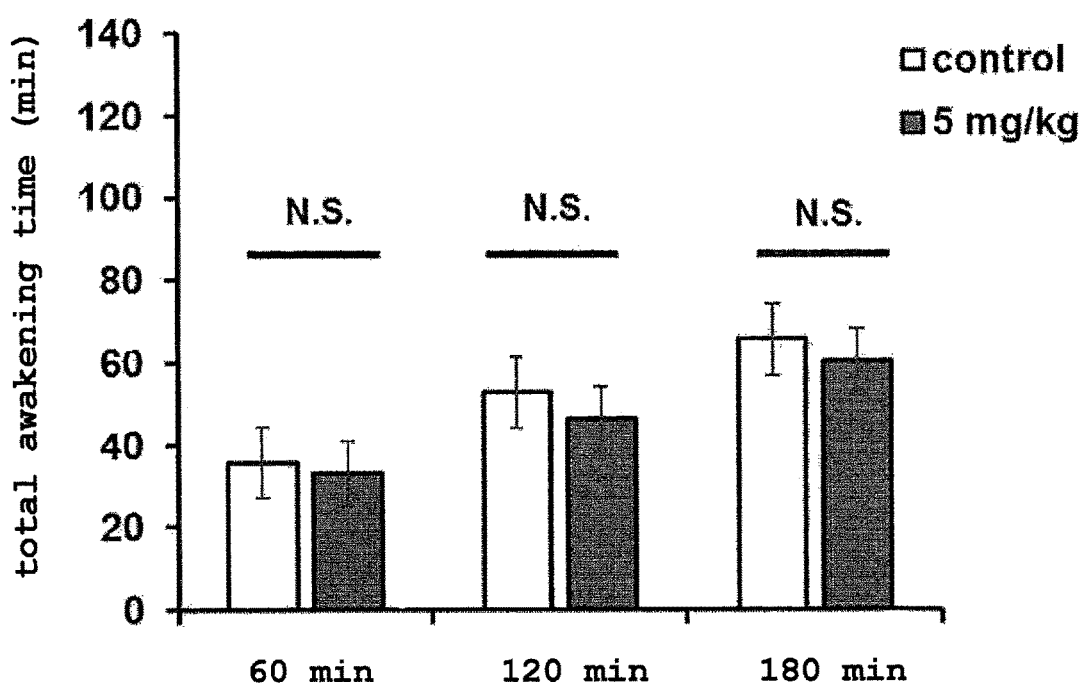
FIG. 2 is a graph showing the results of evaluation (n=3) of the awakening-prolonging effect after oral administration of the test compound (compound of Example 1) in orexin receptor-deficient mice (DKO mice) at 60 min, 120 min, and 180 min after administration. N.S.: not significant

It was confirmed that oral administration of the test compound to WT mice significantly prolonged the awakening time and increased the awakening time in a dose-dependent manner compared to the administration of control MC (FIG. 1), whereas there was no significant difference in the awakening time after administration of control or administration of the test compound to DKO mice (FIG. 2). Typical hypnograms are shown in FIG. 3.

For statistical processing, one-way ANOVA-Bonfferoni test was performed for the control and each concentration of the test compound.

INDUSTRIAL APPLICABILITY

The compound of the present invention shows an orexin 2 receptor agonist activity, and is useful as a prophylactic or therapeutic agent for narcolepsy and the like.

This application is based on patent application No. 2017-238093 filed in Japan, the contents of which are incorporated by reference in full herein.

The invention claimed is:

1. A compound represented by the formula

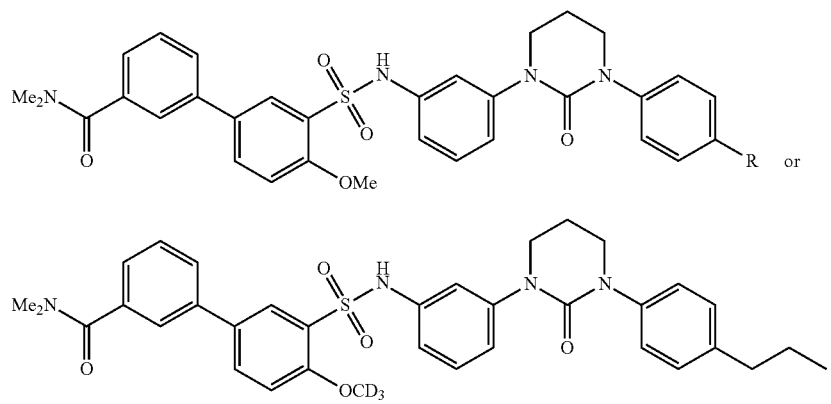

wherein R is propyl, ethyl, isopropyl, methoxy or ethoxy, and Me is methyl,
or a pharmaceutically acceptable acid addition salt thereof.

2. The compound according to claim 1 which is 4'-methoxy-N,N-dimethyl-3'-(N-(3-(2-oxo-3-(4-propylphenyl)tetrahydropyrimidin-1(2H)-yl) phenyl)sulfamoyl)-[1,1'-biphenyl]-3-carboxamide or 4'-(methoxy-d3)-N,N-dimethyl-3'-(N-(3-(2-oxo-3-(4-propylphenyl)tetrahydropyrimidin-1(2H)-yl) phenyl)sulfamoyl)-[1,1'-biphenyl]-3-carboxamide, or a pharmaceutically acceptable acid addition salt thereof.

3. The compound according to claim 1 which is 4'-methoxy-N,N-dimethyl-3'-(N-(3-(2-oxo-3-(4-propylphenyl)tetrahydropyrimidin-1 (2H)-yl)phenyl)sulfamoyl)-[1,1'-biphenyl]-3-carboxamide or a pharmaceutically acceptable acid addition salt thereof.

4. The compound according to claim 1 which is 4'-(methoxy-d3)-N,N-dimethyl-3'-(N-(3-(2-oxo-3-(4-propylphenyl) tetrahydropyrimidin-1(2H)-yl)phenyl)sulfamoyl)-[1,1'-biphenyl]-3-carboxamide or a pharmaceutically acceptable acid addition salt thereof.

5. A medicament comprising the compound according to claim 1 or a pharmaceutically acceptable acid addition salt thereof.

6. An orexin receptor agonist comprising the compound according to claim 1 or a pharmaceutically acceptable acid addition salt thereof.

7. An anti-narcolepsy agent comprising the compound according to claim 1 or a pharmaceutically acceptable acid addition salt thereof.

8. An agent for improving sleepiness comprising the compound according to claim 1 or a pharmaceutically acceptable acid addition salt thereof.

9. A therapeutic agent for obesity, diabetes or depression comprising the compound according to claim 1 or a pharmaceutically acceptable acid addition salt thereof.

10. A method of treating narcolepsy comprising administering an effective amount of the compound according to claim 1 or a pharmaceutically acceptable acid addition salt thereof.

11. A method of improving sleepiness comprising administering an effective amount of the compound according to claim 1 or a pharmaceutically acceptable acid addition salt thereof.

12. A method of treating obesity, diabetes or depression comprising administering an effective amount of the compound according to claim 1 or a pharmaceutically acceptable acid addition salt thereof.

13. A medicament comprising the compound according to claim 2 or a pharmaceutically acceptable acid addition salt thereof.

14. A method of treating narcolepsy comprising administering an effective amount of the compound according to claim 2 or a pharmaceutically acceptable acid addition salt thereof.

15. A method of improving sleepiness comprising administering an effective amount of the compound according to claim 2 or a pharmaceutically acceptable acid addition salt thereof.

16. A method of treating obesity, diabetes or depression comprising administering an effective amount of the compound according to claim 2 or a pharmaceutically acceptable acid addition salt thereof.

* * * * *